United States Patent
Raghu et al.

(10) Patent No.: US 10,346,969 B1
(45) Date of Patent: Jul. 9, 2019

(54) DETECTING SURFACE FLAWS USING COMPUTER VISION

(71) Applicant: Amazon Technologies, Inc., Seattle, WA (US)

(72) Inventors: Aniruddh Raghu, Middlesex (GB); Joseph Rutland, Norfolk (GB); Christian Leistner, Graz (AT); Andres Perez Torres, Cambridgeshire (GB)

(73) Assignee: Amazon Technologies, Inc., Seattle, WA (US)

( * ) Notice: Subject to any disclaimer, the term of this patent is extended or adjusted under 35 U.S.C. 154(b) by 0 days.

(21) Appl. No.: 15/860,607

(22) Filed: Jan. 2, 2018

(51) Int. Cl.
| | |
|---|---|
| *G06K 9/00* | (2006.01) |
| *G06F 15/18* | (2006.01) |
| *H04N 7/18* | (2006.01) |
| *G06T 7/00* | (2017.01) |
| *H04N 5/225* | (2006.01) |

(Continued)

(52) U.S. Cl.
CPC ....... *G06T 7/0008* (2013.01); *G01N 21/8803* (2013.01); *G01N 21/8806* (2013.01); *G01N 21/8851* (2013.01); *G06K 9/4604* (2013.01); *G06K 9/66* (2013.01); *G06T 7/0004* (2013.01); *G06T 7/194* (2017.01); *H04N 5/2256* (2013.01); *G01N 2021/888* (2013.01);

(Continued)

(58) Field of Classification Search
CPC . G06T 7/0004; G06T 7/0008; G01N 21/8806; G01N 21/8803
See application file for complete search history.

(56) References Cited

U.S. PATENT DOCUMENTS

| | | | | |
|---|---|---|---|---|
| 4,895,448 | A | * | 1/1990 | Laird ............... G01B 11/25 356/237.2 |
| 6,622,135 | B1 | * | 9/2003 | Imbert De Tremiolles ........... G06K 9/6276 706/20 |

(Continued)

OTHER PUBLICATIONS

A. Krizhevsky, I. Sutskever, and G. E. Hinton. Imagenet classification with deep convolutional neural networks. NIPS 12 Proceedings of the 25th Int'l Conference on Neural Information Processing Systems (vol. 1), Lake Tahoe, Nevada, pp. 1097-1105, 2012.

(Continued)

*Primary Examiner* — Rebecca A Volentine
(74) *Attorney, Agent, or Firm* — Athorus, PLLC

(57) ABSTRACT

A convolutional neural network may be trained to inspect subjects such as carbon fiber propellers for surface flaws or other damage. The convolutional neural network may be trained using images of damaged and undamaged subjects. The damaged subjects may be damaged authentically during operation or artificially by manual or automated means. Additionally, images of undamaged subjects may be synthetically altered to depict damages, and such images may be used to train the convolutional neural network. Images of damaged and undamaged subjects may be captured for training or inspection purposes by an imaging system having cameras aligned substantially perpendicular to subjects and planar light sources aligned to project light upon the subjects in a manner that minimizes shadows and specular reflections. Once the classifier is trained, patches of an image of a subject may be provided to the classifier, which may predict whether such patches depict damage to the subject.

20 Claims, 17 Drawing Sheets

(51) Int. Cl.
| | |
|---|---|
| *G06K 9/46* | (2006.01) |
| *G06K 9/66* | (2006.01) |
| *G06T 7/194* | (2017.01) |
| *G01N 21/88* | (2006.01) |
| *G06N 3/04* | (2006.01) |
| *G06N 7/00* | (2006.01) |
| *G06Q 10/00* | (2012.01) |

(52) U.S. Cl.
CPC ............... *G06N 3/04* (2013.01); *G06N 7/005* (2013.01); *G06Q 10/20* (2013.01); *G06T 2207/30164* (2013.01)

(56) References Cited

U.S. PATENT DOCUMENTS

| | | | | |
|---|---|---|---|---|
| 2007/0280501 | A1* | 12/2007 | Walton | G01N 21/8806 382/100 |
| 2010/0235037 | A1 | 9/2010 | Vian et al. | |
| 2012/0250010 | A1 | 10/2012 | Hannay | |
| 2014/0067164 | A1 | 3/2014 | Papadopoulos et al. | |
| 2015/0336671 | A1 | 11/2015 | Winn et al. | |
| 2015/0355101 | A1* | 12/2015 | Sun | H04N 13/254 348/46 |
| 2016/0003954 | A1 | 1/2016 | Broussard et al. | |
| 2016/0093124 | A1 | 3/2016 | Shi et al. | |
| 2016/0264262 | A1 | 9/2016 | Colin et al. | |
| 2016/0376031 | A1 | 12/2016 | Michalski et al. | |
| 2017/0328838 | A1* | 11/2017 | Umehara | G01N 21/8803 |
| 2018/0068433 | A1* | 3/2018 | Imakoga | G06T 7/0008 |
| 2018/0322366 | A1* | 11/2018 | Lim | G06K 9/6256 |

OTHER PUBLICATIONS

A. Radford, L. Metz, and S. Chintala. Unsupervised Representation Learning with Deep Convolutional Generative Adversarial Networks. Submitted as Conference Paper for ICLR 2016, San Juan, Puerto Rico, May 2-4, 2016.
A. Shrivastava, T. Pfister, O. Tuzel, J. Susskind, W. Wang, and R. Webb. Learning from Simulated and Unsupervised Images through Adversarial Training. Submitted Nov. 15, 2016, for oral presentation at Conference on Computer Vision and Pattern Recognition (CVPR 2017), Honolulu, Hawaii; presented at CVPR 2017 on Jul. 23, 2017.
B. Zhou, A. Khosla, A. Lapedriza, A. Oliva, and A. Torralba. Learning Deep Features for Discriminative Localization. In Proceedings of the IEEE Conference on Computer Vision and Pattern Recognition (CVPR 2016), Las Vegas, Nevada, pp. 2921-2929, IEEE 2016.
D. Soukup and R. Huber-Mörk. Convolutional Neural Networks for Steel Surface Defect Detection from Photometric Stereo Images, pp. 668-677. Advances in Visual Computing, 10th Int'l Symposium (ISVC 2014), Las Vegas, Nevada, Dec. 8-10, 2014. Springer International Publishing, Switzerland, 2014 (LNCS 8887).
D. Kingma and J. Ba. Adam: A Method for Stochastic Optimization, The Hebrew University of Jerusalem, Advanced Seminar in Deep Learning, Oct. 18, 2015.
D. Kingma and J. Ba. Adam: A method for stochastic optimization. Published at the 3rd International Conference for Learning Representations (ICLR 2015), San Diego, May 9, 2015.
D. Martin. A Practical Guide to Machine Vision Lighting, Advanced Illumination, Rochester, Vt., Feb. 2012.
D. Mery and M.A. Berti. Automatic Detection of Welding Defects Using Texture Features. Insight-Non-Destructive Testing and Condition Monitoring, 45(10):676-681, 2003. Presented at Int'l Symposium on Computed Tomography and Image Processing for Industrial Radiology, Berlin, Germany, Jun. 23-25, 2003.
D. Sammons, W.P. Winfree, E. Burke, and S. Ji. Segmenting delaminations in carbon fiber reinforced polymer composite CT using convolutional neural networks. AIP Conference Proceedings, vol. 1706, p. 110014. American Institute of Physics, AIP Publishing, 2016.
D. Vernon. Machine Vision: Automated Visual Inspection and Robot Vision. Automatica, vol. 30, No. 4, pp. 731-732 (1994), Elsevier Science, Ltd., Great Britain.
D. Wang, A. Khosla, R. Gargeya, H. Irshad, and A. H. Beck. Deep Learning for Identifying Metastatic Breast Cancer. Computer Research Repository (CoRR), Jun. 18, 2016.
G. Wang and T. Liao. Automatic identification of different types of welding defects in radiographic images. NDT&E International, 35(8):519-528 (2002), Elsevier Science Ltd., Great Britain.
H. Raafat and S. Taboun. An Integrated Robotic and Machine Vision System for Surface Flaw Detection and Classification. Computers & Industrial Engineering, Elsevier Science Ltd., Great Britain, 30(1):27-40, 1996.
I. Goodfellow, J. Pouget-Abadie, M. Mirza, B. Xu, D. Warde-Farley, S. Ozair, A. Courville, and Y. Ben-gio. Generative adversarial nets. Advances in Neural Information Processing Systems (NIPS 2014), pp. 2672-2680, 2014.
J. Deng, W. Dong, R. Socher, L.-J. Li, K. Li, and L. Fei-Fei. Imagenet: A large-scale hierarchical image database. In IEEE Conference on Computer Vision and Pattern Recognition, 2009 (CVPR 2009), Miami, Florida, pp. 248-255. IEEE 2009.
J. Long, E. Shelhamer, and T. Darrell. Fully Convolutional Networks for Semantic Segmentation. In Proceedings of the IEEE Conference on Computer Vision and Pattern Recognition (CVPR 2015), Boston, Mass., pp. 3431-3440, IEEE 2015.
J. Masci, U. Meier, D. Ciresan, J. Schmidhuber, and G. Fricout. Steel Defect Classification with Max-Pooling Convolutional Neural Networks. The 2012 International Joint Conference on Neural Networks (IJCNN), Brisbane, Australia, pp. 1-6. IEEE, Jun. 2012.
J. Redmon, S. Divvala, R. Girshick, and A. Farhadi. You Only Look Once: Unified, Real-Time Object Detection. Proceedings of the 2016 IEEE Conference on Computer Vision and Pattern Recognition (CVPR 2016), Las Vegas, Nevada, pp. 779-788, IEEE 2016.
K. He, X. Zhang, S. Ren, and J. Sun. Deep Residual Learning for Image Recognition. In Proceedings of the IEEE Conference on Computer Vision and Pattern Recognition (CVPR 2016), Las Vegas, Nevada, pp. 770-778, IEEE 2016.
K. Simonyan and A. Zisserman. Very Deep Convolutional Networks for Large-Scale Image Recognition. Submitted Sep. 4, 2014, for publication at 3d Int'l Conference on Learning Representations (ICLR 2015), San Diego, California. Presented May 7-9, 2015.
N. Srivastava, G. E. Hinton, A. Krizhevsky, I. Sutskever, and R. Salakhutdinov. Dropout: A Simple Way to Prevent Neural Networks from Overfilling. Journal of Machine Learning Research, 15(1):1929-1958, 2014.
S. Ioffe and C. Szegedy. Batch normalization: Accelerating deep network training by reducing internal covariate shift. In Proceedings of the 32nd International Conference on Machine Learning, Lille, France, pp. 448-456, 2015.
T.-Y. Lin, A. RoyChowdhury, and S. Maji. Bilinear CNN Models for Fine-Grained Visual Recognition. Proceedings of the 2015 IEEE International Conference on Computer Vision (ICCV), Santiago, Chile, pp. 1449-1457, IEEE 2015.
T.-Y. Lin, P. Goyal, R. Girshick, K. He, and P. Dollar. Focal Loss for Dense Object Detection. IEEE International Conference on Computer Vision (2017), pp. 966-974, IEEE 2017.
Y. Gao, O. Beijbom, N. Zhang, and T. Darrell. Compact bilinear pooling. In Proceedings of the IEEE Conference on Computer Vision and Pattern Recognition (CVPR 2016), Las Vegas, Nevada, pp. 317-326, IEEE 2016.
Y. Liu, K. Gadepalli, M. Norouzi, G.E. Dahl, T. Kohlberger, A. Boyko, S. Venugopalan, A. Timofeev, P.Q. Nelson, G.S. Corrado, et al. Detecting Cancer Metastases on Gigapixel Pathology Images. Google Research, Mar. 8, 2017.

\* cited by examiner

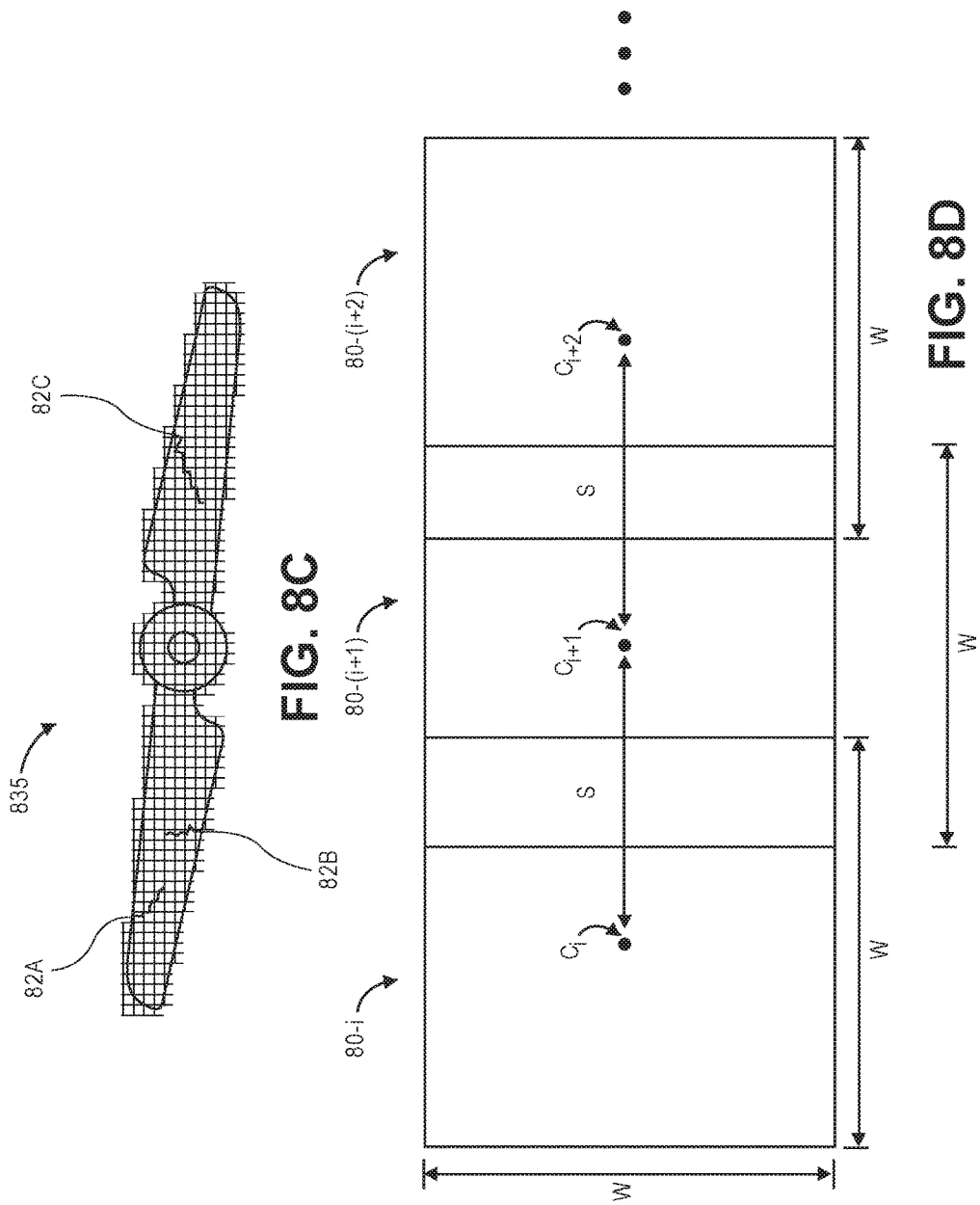

DETECTING SURFACE FLAWS USING COMPUTER VISION

BACKGROUND

Aerial vehicles such as airplanes or helicopters are commonly used to transport people or cargo from an origin to a destination by air. Aerial vehicles may be delicate machines that are formed from lightweight metals, plastics or composites and equipped with motors, rotors or turbofans that are designed to meet or exceed a number of operational constraints or requirements such as speed, altitude or lift. For example, many unmanned aerial vehicles (UAVs, or drones) are built from molded plastic frames and outfitted with electric motors that are powered by onboard batteries or other power sources and configured to rotate propellers for generating lift and/or thrust.

During flight operations, an aerial vehicle may be subject to intense vibrations or oscillations caused by thrusting or lifting forces acting on the aerial vehicle, environmental conditions in an area where the aerial vehicle operates or has operated, shocks or impacts from contact with one or more other objects, or for any other reason. Therefore, from time to time, aerial vehicles are commonly taken out of service for a number of manual or visual inspections. Such inspections are intended to determine whether the strength and integrity of the various components of the aerial vehicle remain sufficient for normal operations. For example, an aerial vehicle may be searched for microfractures, cracks, loosened or broken fasteners, corrosions, fatigue, or evidence of other physical manifestations of stress or strain.

Performing manual or visual inspections typically requires taking an aerial vehicle out of service for extended durations, however. For example, depending on a size of an aerial vehicle, or a length of time since a most recent inspection, a typical inspection of the aerial vehicle may require tens or hundreds of man-hours in order to be completed. Even where a manual or visual inspection results in a determination that the integrity of the aerial vehicle is sound and that the aerial vehicle is operating in a safe and satisfactory manner, the aerial vehicle must still be taken out of service in order to arrive at that determination. Conversely, where an inspection regime calls for manual or visual evaluations to be conducted periodically, e.g., after a predetermined number of hours have lapsed or missions have been completed, such evaluations are unable to determine when an operational issue arises between such periodic inspections, and implementing a remedy for the operational issue is necessarily delayed. Every hour in which an aerial vehicle is out-of-service is an hour in which the aerial vehicle is not providing value.

BRIEF DESCRIPTION OF THE DRAWINGS

FIGS. 8A through 8F are views of aspects of one system for detecting surface flaws using computer vision in accordance with embodiments of the present disclosure.

DETAILED DESCRIPTION

As is set forth in greater detail below, the present disclosure is directed to automatically inspecting subjects such as propellers of aerial vehicles using computer vision techniques. In some embodiments, a plurality of high-resolution images of a propeller or other subject may be captured while the propeller is stationary or in motion. For example, the subject may be placed within an imaging system having cameras or other imaging devices for capturing images of one or more sides of the subject as well as planar light sources for illuminating surfaces of the subject in a manner that minimizes specular reflections on such surfaces. Alternatively, images may be captured of the propeller when the propeller is mounted to a motor of an aerial vehicle, while the propeller is stationary or in motion. The images may be processed by defining a plurality of overlapping patches, and each of the patches may be provided to a trained neural network or other classifier to determine whether such patches depict any surface flaws. The neural network may be trained using labeled patches extracted from images of propellers that are damaged authentically (e.g., where a propeller is damaged during operation according to one or more normal, standard or accepted operating procedures), propellers that are damaged artificially (e.g., where a propeller is intentionally damaged while not in operation according to one or more normal, standard or accepted operating procedures) or propellers that are damaged synthetically (e.g., where an appearance of a propeller within an image is synthetically altered to depict or emphasize damages), along with labeled patches extracted from images of undamaged propellers.

Figure 1A:
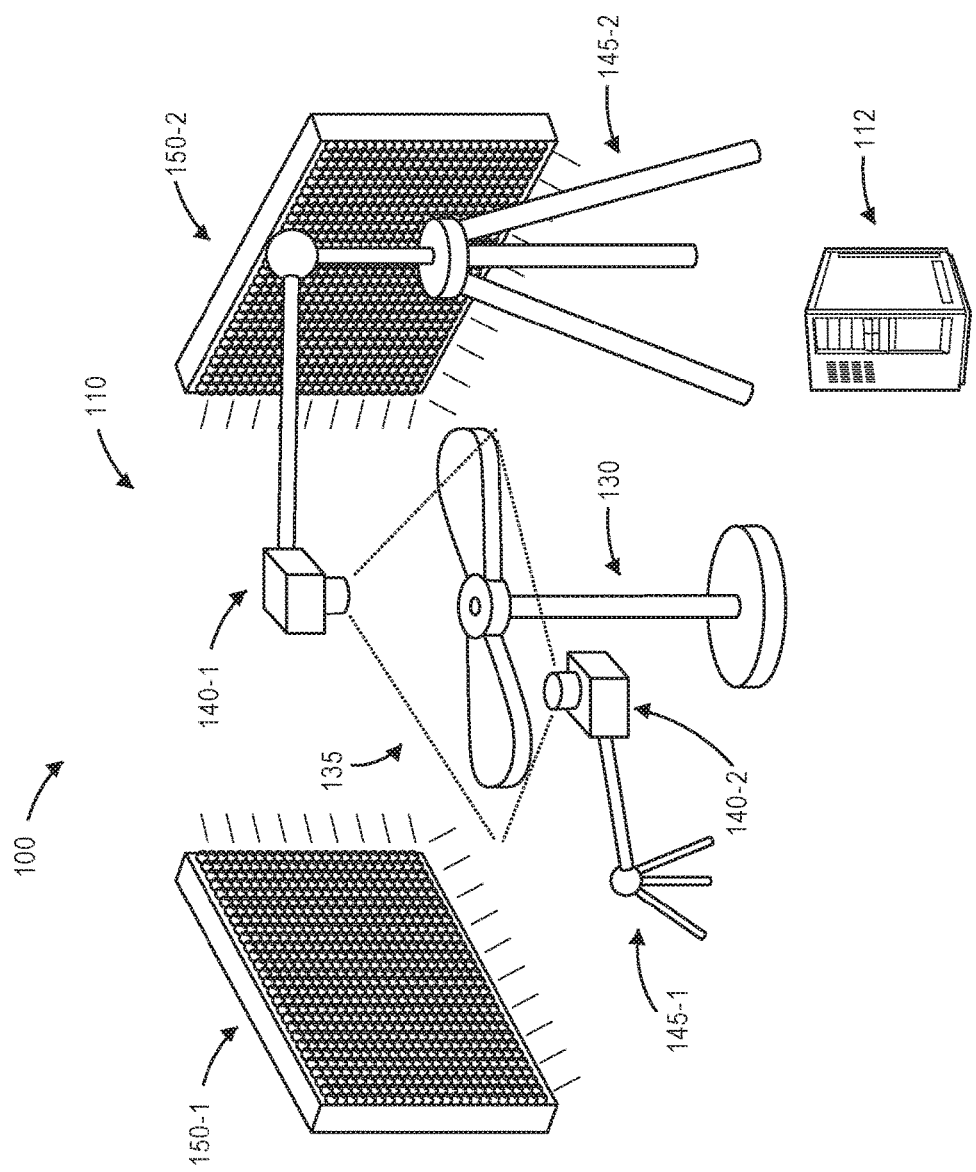
FIGS. 1A and 1B are views of aspects of one system for detecting surface flaws using computer vision in accordance with embodiments of the present disclosure.
Figure 1B:
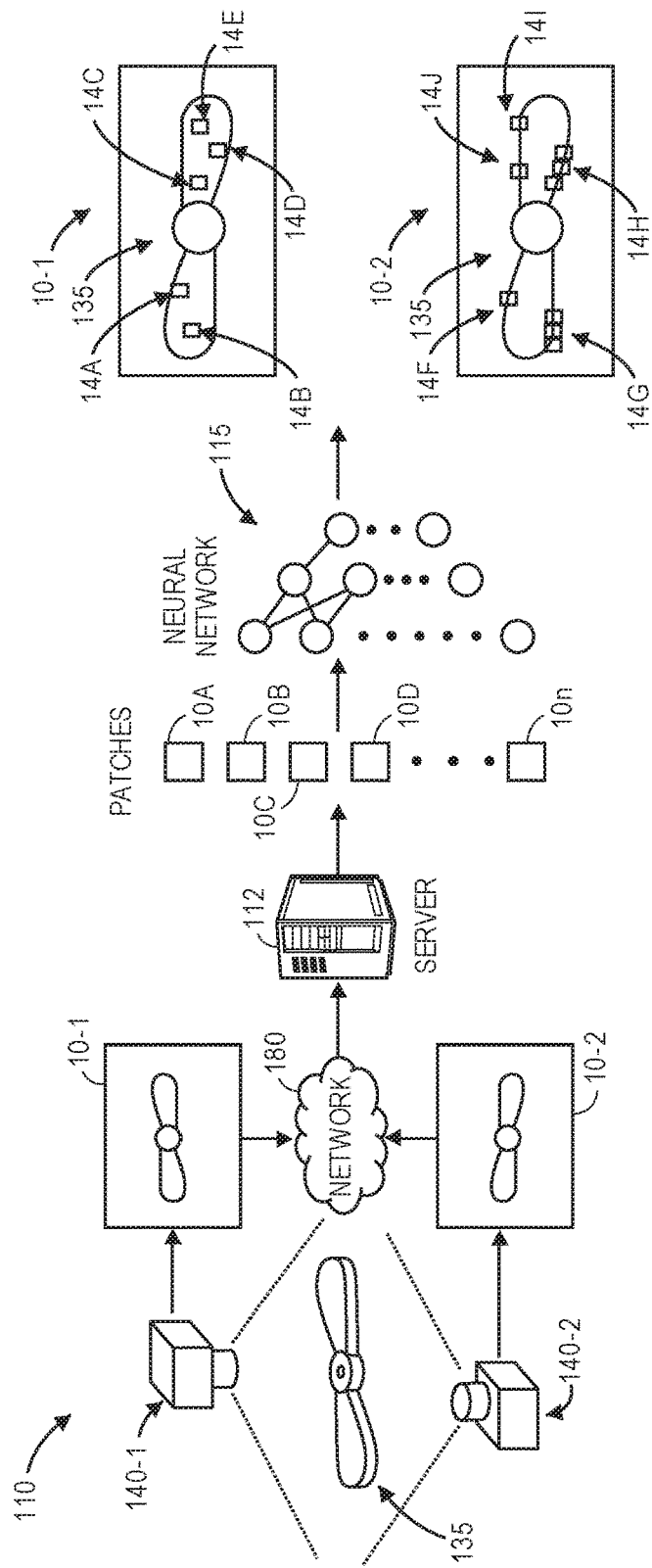

Referring to FIGS. 1A and 1B, views of aspects of one system for detecting surface flaws using computer vision are shown. As is shown in FIG. 1A, the system 100 includes an imaging system 110 having a subject mount 130, a pair of imaging devices 140-1, 140-2 (e.g., digital cameras) and a pair of light sources 150-1, 150-2. The subject mount 130 includes a subject 135 (viz., a two-bladed propeller) fixedly or rotatably mounted thereto, e.g., about a hub or other central portion of the subject 135. For example, the subject mount 130 may include a fixed extension for supporting the subject 135 within fields of view of one or more of the imaging devices 140-1, 140-2, e.g., in a fixed position and/or a fixed orientation. Alternatively, the subject mount 130 may include one or more motors or other components for varying a position and/or alignment of the subject 135 within the fields of view of one or more of the imaging devices 140-1, 140-2. For example, the subject mount 130 may be configured to rotate the subject 135 at any rotational speed. In some embodiments, the subject 135 may be positioned and/or oriented within the fields of view of the imaging devices 140-1, 140-2 using one or more systems or components that are not exclusively limited to imaging or inspection operations. For example, where the subject 135 is a propeller or another aspect of an aerial vehicle (e.g., a frame, a control surface), the aerial vehicle may be positioned at the imaging system 110 in a manner that causes the subject 135 to be positioned and/or aligned in a desired manner within the fields of view of the imaging devices 140-1, 140-2. In some embodiments, the imaging devices 140-1, 140-2 may capture images of the subject 135 as the subject 135 is stationary or rotating, e.g., at normal operating speeds.

The imaging devices 140-1, 140-2 of FIG. 1A are each mounted to tripods 145-1, 145-2 and aligned to capture imaging data regarding objects placed within their common field of view, such as the subject 135. In some embodiments, one or both of the imaging devices 140-1, 140-2 may be a digital single-lens reflex (or "DSLR") camera having a resolution of approximately twenty-eight megapixels (28 MP), a focal length of approximately twenty-eight millimeters (28 mm), an f-stop value of f/8, an exposure value of +2, a sensitivity of ISO 100, and a variable shutter speed. Any type or form of imaging device may be utilized in accordance with the present disclosure, however.

As is shown in FIG. 1A, the subject 135 includes a plurality of substantially flat faces, and is mounted to the subject mount 130 at a hub or other central portion thereof, such that one or more faces of the subject 135 are oriented substantially normal to axes of orientation of each of the imaging devices 140-1, 140-2, e.g., above and below the faces of the subject 135. For example, as is shown in FIG. 1A, the axes of orientation of the imaging devices 140-1, 140-2 are substantially parallel to one another, and aligned in opposite directions, e.g., with the imaging device 140-1 aligned in a substantially downward orientation and the imaging device 140-2 aligned in a substantially upward orientation. Accordingly, all or much of the faces of the subject 135 may each appear within a common depth of field of the respective imaging devices 140-1, 140-2, and imaging data (e.g., digital images) captured by the imaging devices 140-1, 140-2 may be processed to determine whether the subject 135 includes one or more surface flaws or other damage.

As is shown in FIG. 1A, the light sources 150-1, 150-2 are directionally diffuse and feature substantially planar constructions or configurations. The light sources 150-1, 150-2 are configured to project light onto surfaces of the subject 135 from diffuse angles. For example, as is shown in FIG. 1A, the light sources 150-1, 150-2 include a plurality of individual lights or illuminators (e.g., bulbs, light-emitting diodes, or the like) that are aligned to project light upon the subject 135 at angles that are nearly perpendicular to the axes of orientation of the imaging devices 140-1, 140-2. For example, axes normal to the planar constructions or configurations of the light sources 150-1, 150-2 are substantially parallel to surfaces of the subject 135, and nearly or substantially perpendicular to axes of orientation of the imaging devices 140-1, 140-2. In some embodiments, an angle between the axes normal to the planar constructions or configurations of the light sources 150-1, 150-2 is greater than or equal to forty-five degrees (45°), greater than or equal to sixty degrees (60°), or nearly ninety degrees (90°). Alternatively, the light sources 150-1, 150-2 may include lights or illuminators that are arranged in non-planar constructions or configurations, e.g., one or more sections having shapes in the form of portions of spheres (e.g., spherical caps or domes), ellipsoids, or any other sections.

The orientations of the light sources 150-1, 150-2 with respect to the subject 135 and the imaging devices 140-1, 140-2 may improve the quality of imaging data captured by the respective imaging devices 140-1, 140-2 in at least two respects. For example, by providing a plurality of discrete lights or illuminators distributed throughout the light sources 150-1, 150-2, rather than a single bulb or other source, and by orienting the light sources 150-1, 150-2 substantially normal to the axes of orientation of the imaging devices 140-1, 140-2, points of specular reflection (or specularities) appearing on surfaces of the subject 135 within imaging data captured by the imaging devices 140-1, 140-2 are infinitesimal and/or substantially invisible, thereby enhancing the quality and value of imaging data captured thereby. Furthermore, where the light sources 150-1, 150-2 are aligned on different sides or from different perspectives with respect to the subject 135, e.g., from a left side and a right side of the subject 135, such as is shown in FIG. 1A, shadowing or other adverse visual effects may also be minimized.

In accordance with some embodiments of the present disclosure, imaging data captured from the subject 135 may be used to train a classifier, e.g., a convolutional neural network, to determine whether the imaging data depicts one or more flaws within surfaces of the subject 135, or analyzed using a classifier that has been trained accordingly. Imaging systems such as the imaging system 110 of FIG. 1A may be used to capture imaging data from subjects (e.g., damaged and/or undamaged subjects) in a training mode or in an operational mode, e.g., to train a classifier to recognize surface flaws or, alternatively, to determine whether the subject includes any surface flaws based on outputs received from the trained classifier.

As is shown in FIG. 1B, the imaging devices 140-1, 140-2 may capture a plurality of images 10-1, 10-2 from above and below the subject 135, respectively, and the images 10-1, 10-2 may be processed to determine whether the subject 135 contains any surface flaws or other damage. In some embodiments, the images 10-1, 10-2 may be of a megapixel scale and have substantially high levels of resolution. The images 10-1, 10-2 may be transferred to a server 112 directly or by way of a network 180, e.g., by a wired or wireless connection. For example, the server 112 may be configured to extract a plurality of patches 10A, 10B, 10C, 10D . . . 10n from the images 10-1, 10-2, and to identify patches that include foreground data (e.g., patches depicting portions of the subject 135) rather than background data (e.g., patches depicting objects other than the subject 135, such as the subject mount 130 and/or any surfaces or features to which the subject mount 130 is installed). Patches of the images 10-1, 10-2 that are identified as depicting portions of the subject 135 may be provided to a convolutional neural network 115 or other classifier that is trained to classify such patches, e.g., to determine whether the portions of the subject 135 depicted within such patches include one or more surface flaws. The convolutional neural network 115 may include any number of layers of neurons or nodes, e.g., an input layer, an output layer, and one or more hidden layers, each of which may be trained to recognize aspects of flaws within one or more of the patches depicting portions of the subject 135 in the images 10-1, 10-2.

Based on outputs received from the convolutional neural network 115, a map of locations 14A, 14B, 14C, 14D, 14E of surface flaws on the subject 135 may be represented on the image 10-1, and a map of locations 14F, 14G, 14H, 14I, 14J of surface flaws on the subject 135 may be represented on the images 10-1, 10-2.

Accordingly, the systems and methods of the present disclosure may be utilized to automate and regulate the performance of inspections of subjects, including but not limited to one or more components of aerial vehicles. In particular, such systems and methods may replace traditional periodic manual or visual inspections with automatic inspections that are conducted based on imaging data captured using one or more high-resolution imaging devices. The automatic inspections may be conducted by providing the imaging data to one or more trained classifiers, e.g., convolutional neural networks. In some embodiments, the classifier may be a convolutional neural network with bilinear pooling, such as a very deep convolutional network configured for large-scale image recognition. For example, an output of a final convolutional layer of the convolutional neural network may be extracted and batch normalizations may be applied to the output, with a bilinear pooling operation performed on the normalized output. Any type or form of trainable classifier, e.g., any type of convolutional neural network, may be utilized in accordance with the present disclosure.

In accordance with embodiments of the present disclosure, subjects may be evaluated at any time within a life span or operating cycle for the respective subjects. In some embodiments, one or more of the systems and methods disclosed herein may be used to perform quality assurance testing on one or more subjects, e.g., on representative samples of a large number of such subjects following their manufacture or assembly, in order to determine that such subjects are properly manufactured or whether processes for manufacturing such subjects are valid. For example, where carbon fiber propellers are mass-produced according to a common procedure, a predetermined number of the carbon fiber propellers may be randomly selected and photographed in order to confirm that propellers manufactured according to the procedure are properly manufactured and free from surface flaws. Alternatively, a subject may be inspected at regular times or intervals, or following one or more events. For example, when an aerial vehicle returns from performing a mission, or when the aerial vehicle is between two phases of operation, one or more aspects of the aerial vehicle (e.g., propellers, control surfaces or the like) may be photographed, and the images may be processed to determine whether the aerial vehicle is in a satisfactory, airworthy condition, whether the aerial vehicle is experiencing any structural deficiencies (e.g., microfractures, cracks, loosened or broken fasteners, corrosions, fatigue, other physical manifestations of stress or strain), or whether maintenance, repairs or further inspections may be required. Additionally, one or more inspections of subjects may be performed again and again, as necessary, e.g., after each use of such subjects, between any two uses of such subjects, or in accordance with a predetermined schedule.

Aerial vehicles are typically evaluated from time to time for failures or deficiencies in materials and components. Because aerial vehicles commonly radiate noise and/or other vibrations in response to thrust or lift forces, flow conditions, impacts or other adverse events, aerial vehicles must be routinely inspected to properly assess risks of failure of a specific component, of the aerial vehicle as a whole, or of aerial vehicles in a fleet. Whether conditions or deficiencies such as microfractures, cracks, fractured fasteners, corrosions, fatigue, or other adverse conditions exist on an aerial vehicle may be assessed with respect to structural components, control surfaces, motors or rotors or appurtenances such as landing gear. In particular, structural joints on aerial vehicles, e.g., concentrated locations where loads and stresses are transferred from one component to another, such as by fasteners, are particularly susceptible to cracks or other indicia of fatigue. For example, relative movement between structural details and fasteners, as well as stress concentrations, may cause, enable or exacerbate microfractures, corrosions or cracking within such fasteners or structural details, such as fuselage skins or other components. If left untreated, microfractures, corrosions or cracking may lead to serious structural failures of the structural details or fasteners, or the aerial vehicle as a whole.

Machine learning tools, such as artificial neural networks, have been utilized to identify relations between respective elements of apparently unrelated sets of data. An artificial neural network is a parallel distributed computing processor system comprised of individual units that may collectively learn and store experimental knowledge, and make such knowledge available for use in one or more applications. Such a network may simulate the non-linear mental performance of the many neurons of the human brain in multiple layers by acquiring knowledge from an environment through one or more flexible learning processes, determining the strengths of the respective connections between such neurons, and utilizing such strengths when storing acquired knowledge. Like the human brain, an artificial neural network may use any number of neurons in any number of layers, including an input layer, an output layer, and one or more intervening hidden layers. In view of their versatility, and their inherent mimicking of the human brain, machine learning tools including not only artificial neural networks but also nearest neighbor methods or analyses, factorization methods or techniques, K-means clustering analyses or techniques, similarity measures such as log likelihood similarities or cosine similarities, latent Dirichlet allocations or other topic models, or latent semantic analyses have been utilized in image processing applications.

Artificial neural networks may be trained to map inputted data to desired outputs by adjusting the strengths of the connections between one or more neurons, which are sometimes called synaptic weights. An artificial neural network may have any number of layers, including an input layer, an output layer, and any number of intervening hidden layers. Each of the neurons in a layer within a neural network may receive an input and generate an output in accordance with an activation or energy function, with parameters corresponding to the various strengths or synaptic weights. For example, in a heterogeneous neural network, each of the neurons within the network may be understood to have different activation or energy functions. In some neural networks, at least one of the activation or energy functions may take the form of a sigmoid function, wherein an output thereof may have a range of zero to one or 0 to 1. In other neural networks, at least one of the activation or energy functions may take the form of a hyperbolic tangent function, wherein an output thereof may have a range of negative one to positive one, or −1 to +1. Thus, the training of a neural network according to an identity function results in the redefinition or adjustment of the strengths or weights of such connections between neurons in the various layers of the neural network, in order to provide an output that most closely approximates or associates with the input to the maximum practicable extent.

Artificial neural networks may typically be characterized as either feedforward neural networks or recurrent neural networks, and may be fully or partially connected. In a feedforward neural network, e.g., a convolutional neural network, information may specifically flow in one direction from an input layer to an output layer, while in a recurrent neural network, at least one feedback loop returns information regarding the difference between the actual output and the targeted output for training purposes. Additionally, in a fully connected neural network architecture, each of the neurons in one of the layers is connected to all of the neurons in a subsequent layer. By contrast, in a sparsely connected neural network architecture, the number of activations of each of the neurons is limited, such as by a sparsity parameter.

Moreover, the training of a neural network is typically characterized as supervised or unsupervised. In supervised learning, a training set comprises at least one input and at least one target output for the input. Thus, the neural network is trained to identify the target output, to within an acceptable level of error. In unsupervised learning of an identity function, such as that which is typically performed by a sparse autoencoder, target output of the training set is the input, and the neural network is trained to recognize the input as such. Sparse autoencoders employ backpropagation in order to train the autoencoders to recognize an approximation of an identity function for an input, or to otherwise approximate the input. Such backpropagation algorithms may operate according to methods of steepest descent, conjugate gradient methods, or other like methods or techniques, in accordance with the systems and methods of the present disclosure. Those of ordinary skill in the pertinent art would recognize that any algorithm or method may be used to train one or more layers of a neural network. Likewise, any algorithm or method may be used to determine and minimize errors in an output of such a network. Additionally, those of ordinary skill in the pertinent art would further recognize that the various layers of a neural network may be trained collectively, such as in a sparse autoencoder, or individually, such that each output from one hidden layer of the neural network acts as an input to a subsequent hidden layer.

Once a neural network has been trained to recognize dominant characteristics of an input of a training set, e.g., to associate an image with a label to within an acceptable tolerance, an input in the form of an image may be provided to the trained network, and a label may be identified based on the output thereof.

The systems and methods of the present disclosure are directed to performing inspections of subjects on an automated basis using imaging data captured from such subjects, which may include but are not limited to propellers for use aboard aerial vehicles (e.g., unmanned aerial vehicles, or drones). The systems and methods disclosed herein enable traditional, periodic and/or manual inspections of aerial vehicles to be performed by capturing imaging data from such subjects and providing the imaging data as inputs to one or more trained classifiers, e.g., convolutional neural networks. Whether a subject includes any number of surface flaws, or whether any failures in blades, bearings, surfaces or rotating components are imminent, may be determined based on outputs received from such classifiers.

Using one or more machine learning systems or tools, e.g., a trained classifier, such as a convolutional neural network, imaging data captured by one or more imaging devices may be interpreted in order to determine whether such imaging data is representative or indicative of one or more pending or emerging structural deficiencies, such as microfractures, cracks, loosened or broken fasteners, corrosions, fatigue, or evidence of other physical manifestations of stress or strain in one or more subjects, e.g., components of an aerial vehicle. Moreover, the machine learning systems or tools of the present disclosure may operate in a number of phases or modes.

First, in a training phase or mode, a machine learning system, or one or more computing devices or machines on which the system resides or operates, may receive imaging data captured from a plurality of damaged and undamaged subjects. Some of the damaged subjects may have been authentically damaged during normal operations. For example, where one or more of such subjects is a propeller used on an aerial vehicle, some of the subjects may have been authentically damaged in flight, e.g., by contact with grasses, stones or other objects, which may cause edge indentations, delaminations or other physical effects on outer surfaces of the propeller. Additionally, some of the damaged subjects may have been artificially damaged, i.e., using hammers, drills, awls or other manually or automatically operated tools, which may also impart physical effects on outer surfaces of the propeller.

After imaging data has been captured from a number of undamaged subjects, some of the images of undamaged subjects may be synthetically altered to include simulated surface flaws, e.g., by altering portions of such subjects within the images with synthetic markings indicative of damage thereon. Moreover, once images of undamaged subjects have been synthetically altered to indicate damage, such images may be refined to enhance the appearance of damage within such images, and make such images appear to be more realistic. For example, a synthetically altered image may be provided to a generative adversarial network, or GAN, to enhance the realism of the synthetic damage imparted upon such images. In some embodiments, a generative adversarial network may refine such images using a refiner network that is configured to make a synthetically altered image appear more realistic, and a discriminator network that is configured to distinguish between synthetic images and real images. Synthesizing damage within images of undamaged subjects is substantially less expensive than artificially damaging undamaged subjects and capturing imaging data from such subjects.

After a plurality of images of undamaged subjects and damaged subjects have been identified or captured, the images may be subject to one or more annotation processes in which regions of such images that depict damage to the subjects, such as authentic damage, artificial damages or synthetic damage, are designated accordingly. In computer vision applications, annotation is commonly known as marking or labeling of images or video files (e.g., sequences of one or more image frames) captured from a scene, such as to denote the presence and location of one or more objects or other features within the scene in the images or video files. Annotating an image or a video file typically involves placing a virtual marking such as a box (e.g., a bounding box) or other shape on the image, or on an image frame of a video file, thereby denoting that the image or image frame depicts an item, or includes pixels of significance, within the box or shape. Alternatively, a video file may be annotated by applying markings or layers including alphanumeric characters, hyperlinks or other markings on specific frames of the video file, thereby enhancing the functionality or interactivity of the video file in general, or of the video frames in particular. In some embodiments, a record of one or more annotations that are made to an image or a video file may be maintained separately, e.g., in a discrete file, that identifies the image or an image frame of the video file to which the annotations have been made, as well as locations of one or more aspects of the annotations within the image or image frame, e.g., pixels or coordinates of one or more borders, vertices or other features of such annotations. In some other embodiments, the record of the one or more annotations may be stored within an image or a video file itself, e.g., as metadata that accompanies or is stored in association with the image or the video file.

Images of undamaged subjects and damaged subjects may be processed in order to extract patches of predetermined sizes or shapes therefrom. In some embodiments, foreground and/or background portions of an image may be identified by adaptive thresholding, e.g., by Otsu binarization, and a plurality of overlapping patches may be defined in a grid and extracted from the foreground portions. In some implementations, a grid of patches, each of which is four hundred pixels by four hundred pixels in size, and has an overlapping stride of approximately three hundred pixels, may be extracted from the foreground portions of the images.

In some embodiments, each of the patches may be labeled as "damaged" or "undamaged" based on whether some or all of the patches depicts a surface flaw or other form of damage. For example, a patch may be identified as damaged if a border of the patch intersects an annotation of a surface flaw or a damage applied to an image from which the patch was extracted. Alternatively, each of the patches may be specifically annotated after the patches have been extracted from an image.

A data set may be defined by labeled patches extracted from images of authentically damaged subjects, artificially damaged subjects, synthetically damaged subjects and undamaged subjects. The images and labels of the data set may be subdivided into a training set and a validation set, with the images and labels of the training set being used to train a machine learning tool, e.g., a classifier, such as a convolutional neural network, to recognize damage in one or more images, and the images and labels of the validation set being used to test or confirm the validity of the trained machine learning tool.

Figure 2A:
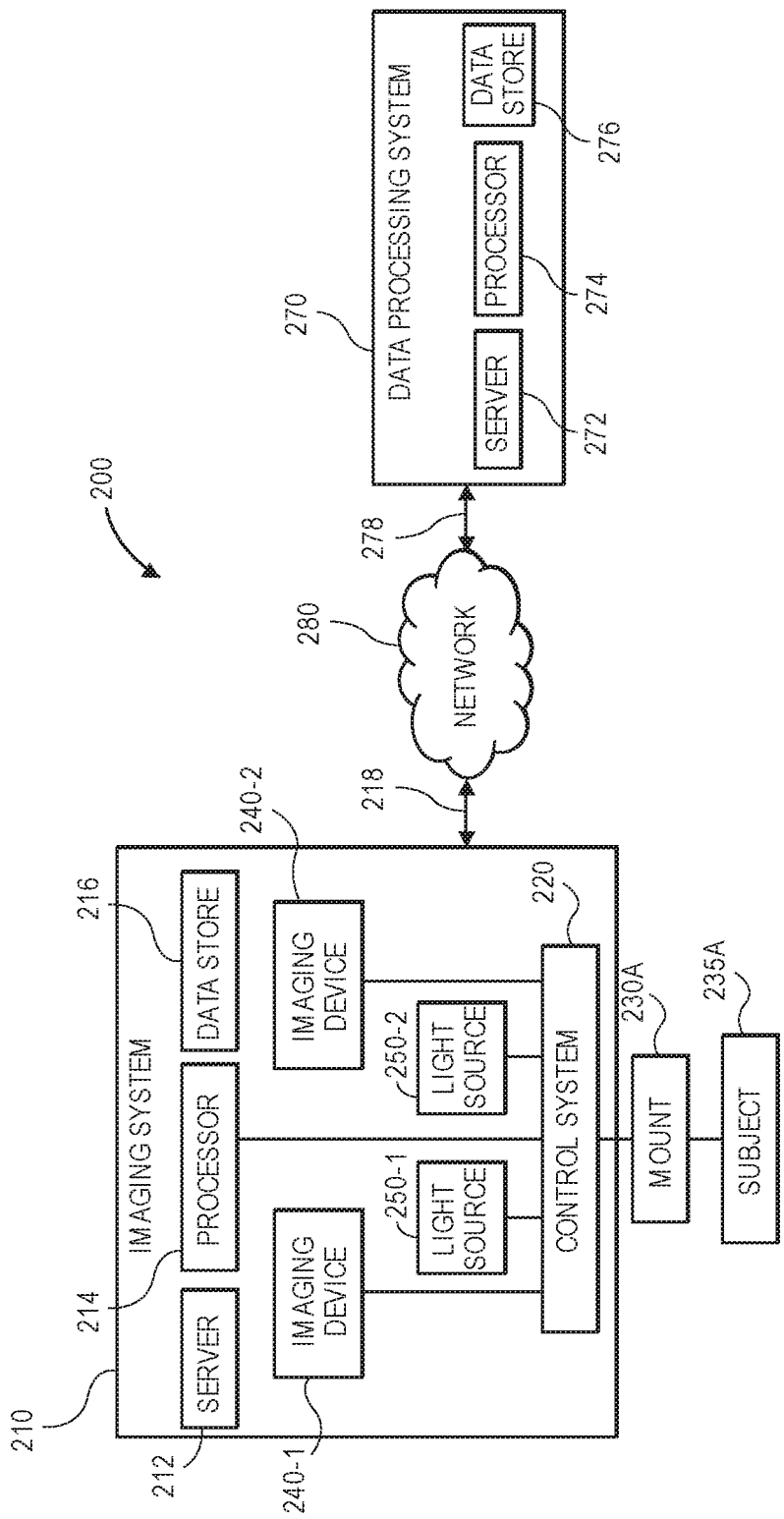
FIGS. 2A and 2B are block diagrams of one system for detecting surface flaws using computer vision in accordance with embodiments of the present disclosure.
Figure 2B:
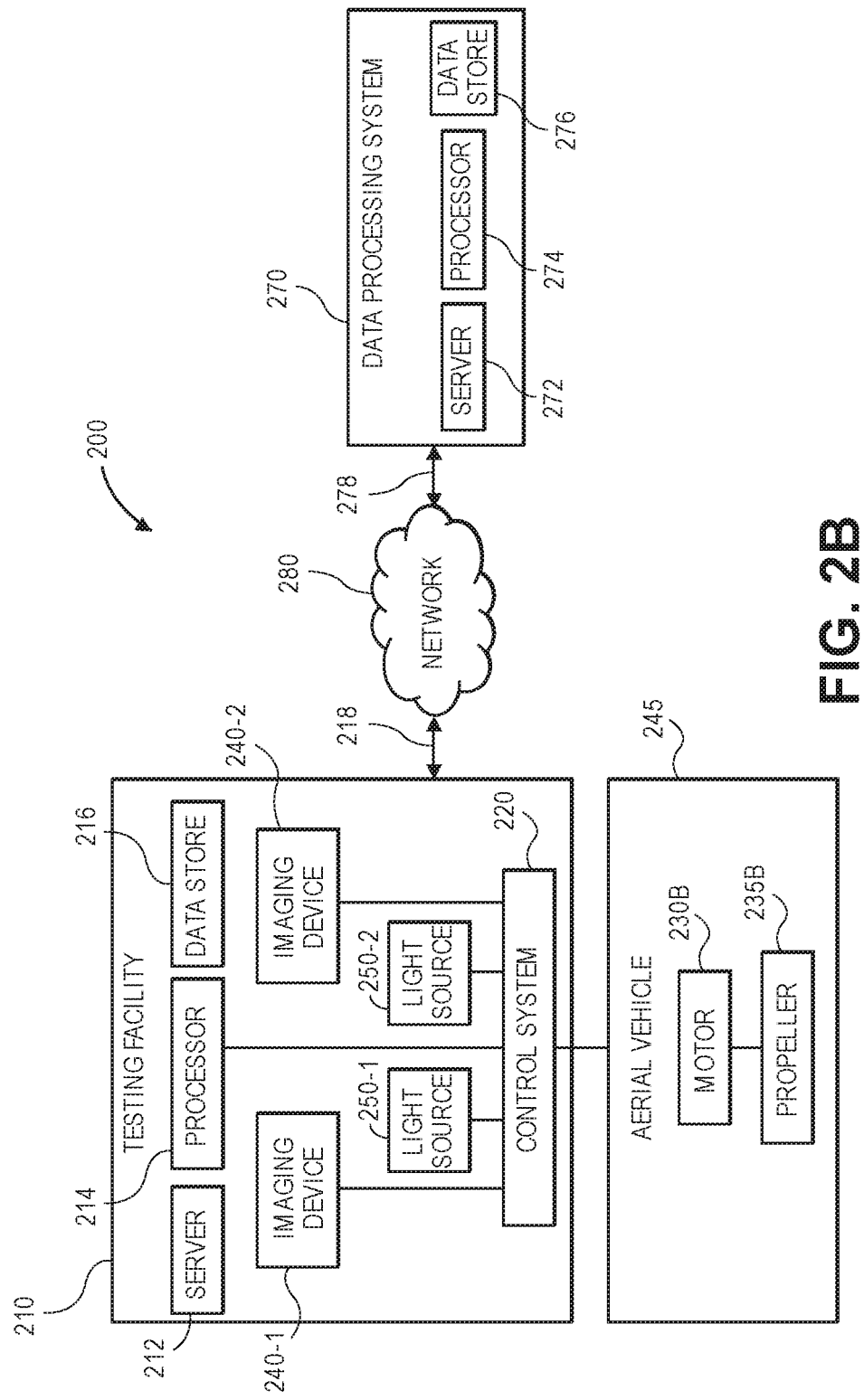

Referring to FIGS. 2A and 2B, block diagrams of one system 200 for detecting surface flaws using computer vision in accordance with embodiments of the present disclosure is shown. As is shown in FIG. 2A, the system 200 includes an imaging system 210 and a data processing system 270 connected to one another over a network 280. Except where otherwise noted, reference numerals preceded by the number "2" shown in the block diagram of FIG. 2A or 2B indicate components or features that are similar to components or features having reference numerals preceded by the number "1" shown in FIGS. 1A and 1B.

The imaging system 210 includes a server 212, a processor 214, a data store 216, a control system 220, a plurality of imaging devices 240-1, 240-2, and a plurality of light sources 250-1, 250-2. The imaging system 210 is configured to capture imaging data of any type or form regarding a subject 235A, which may be fixedly or movably mounted or otherwise coupled to a mount 230A and provided within a field of view of one or more of the imaging devices 240-1, 240-2.

The imaging system 210 may be any facility, structure, station or other location where one or more inspections may be performed on one or more subjects, e.g., the subject 235A, such as a propeller of an aerial vehicle. In some embodiments, the imaging system 210 may be provided in association with one or more facilities, structures, stations or locations associated with one or more missions to be performed by aerial vehicles, e.g., delivery or surveillance operations. The imaging system 210 may be provided within or as a part of one or more independent or freestanding facilities, structures, stations or locations that need not be associated with any one specific mission.

As is shown in FIG. 2A, the imaging system 210 includes one or more physical or virtual computer servers 212 having a plurality of processors 214 provided for any specific or general purpose, and at least one data store (e.g., one or more databases) 216 associated therewith. For example, the servers 212, the processors 214 and/or the data stores 216 of FIGS. 2A and 2B may be independently provided for the exclusive purpose of receiving, analyzing or storing imaging data and/or associated audio signals or other data captured by the one or more imaging devices 240-1, 240-2 or, alternatively, provided in connection with one or more physical or virtual services that are configured to receive, analyze or store such data, or perform any other functions. The servers 212 may be connected to or otherwise communicate with the processors 214 and/or the data stores 216, which may store any type of information or data, including but not limited to imaging data and/or attributes, descriptions, annotations or other information regarding imaging data (e.g., inspection results), for any purpose. The servers 212 and/or the processors 214 may also connect to or otherwise communicate with the network 280, as indicated by line 218, through the sending and receiving of digital data.

The processors 214 may be a uniprocessor system including one processor, or a multiprocessor system including several processors (e.g., two, four, eight, or another suitable number), and may be capable of executing instructions. For example, in some embodiments, the processor 214 may be a general-purpose or embedded processor implementing any of a number of instruction set architectures (ISAs), such as the x86, PowerPC, SPARC, or MIPS ISAs, or any other suitable ISA. Where the processor 214 is a multiprocessor system, each of the processors within the multiprocessor system may operate the same ISA, or different ISAs.

Additionally, the data stores 216 (or other memory or storage components) may store any type of information or data, e.g., instructions for operating the imaging system 210, or information or data captured during operations of the imaging system 210. The data stores 216 may be implemented using any suitable memory technology, such as static random-access memory (SRAM), synchronous dynamic RAM (SDRAM), nonvolatile/Flash-type memory, or any other type of memory. In some embodiments, program instructions, imaging data and/or other data items may be received or sent via a transceiver, e.g., by transmission media or signals, such as electrical, electromagnetic, or digital signals, which may be conveyed via a communication medium such as a wired and/or a wireless link.

In some embodiments, the servers 212, the processors 214 and/or the data stores 216 may be provided in a physical location, e.g., a common physical location of one or more of the imaging devices 240-1, 240-2 and/or one or more of the light sources 250-1, 250-2. In other such embodiments, the servers 212, the processors 214 and/or the data stores 216 may be provided in one or more alternate or virtual locations, e.g., a different physical location from one or more of the imaging devices 240-1, 240-2 and/or one or more of the light sources 250-1, 250-2, or in a "cloud"-based environment.

In addition to the servers 212, the processors 214 and/or the data stores 216, the imaging system 210 may further include any number of other components, including but not limited to one or more transceivers that are configured to enable the imaging system 210 to communicate through one or more wired or wireless means, e.g., wired technologies such as Universal Serial Bus (or "USB") or fiber optic cable, or standard wireless protocols such as Bluetooth® or any Wireless Fidelity (or "Wi-Fi") protocol, such as over the network 280 or directly. Such transceivers may enable the testing system 210 to communicate through one or more wired technologies such as Universal Serial Bus (or "USB") or fiber optic cable, or standard wireless protocols such as Bluetooth® or any Wireless Fidelity (or "Wi-Fi") protocol, such as over the network 280 or directly. Such transceivers may further include or be in communication with one or more input/output (or "I/O") interfaces, network interfaces and/or input/output devices, and may be configured to allow information or data to be exchanged between one or more of the components of the imaging system 210, or to one or more other computer devices or systems (e.g., other aerial vehicles, not shown) via the network 280. For example, in some embodiments, a transceiver may be configured to coordinate I/O traffic between the servers 212 and/or processors 214 and one or more onboard or external computer devices or components. Such transceivers may perform any necessary protocol, timing or other data transformations in order to convert data signals from a first format suitable for use by one component into a second format suitable for use by another component. In some embodiments, transceivers may include support for devices attached through various types of peripheral buses, e.g., variants of the Peripheral Component Interconnect (PCI) bus standard or the Universal Serial Bus (USB) standard. In some other embodiments, functions ordinarily performed by transceivers may be split into two or more separate components, or integrated with the servers 212 and/or the processors 214.

The control system 220 may include one or more controllers and/or power supplies for controlling the operation of the control system 220, the mount 230A, the imaging devices 240-1, 240-2 and/or the light sources 250-1, 250-2. For example, the control system 220 may be configured to cause or control the mount 230A to position the subject 235A within the imaging system 210, or to rotate or translate the subject 235A at desired speeds, and to cause one or more of the imaging devices 240-1, 240-2 to capture any imaging data (e.g., still or moving images) of the subject 235A along with any associated audio data and/or metadata. The control system 220 may further control other aspects of the imaging system 210. In some embodiments, the control system 220 may be integrated with one or more of the server 212, the processor 214 and/or the data store 216.

The mount 230A may be any structure or support for maintaining physical control of the subject 235A in any static or dynamic fashion. For example, in some embodiments, the mount 230A may be an unmotorized stand, clamp, stanchion, column, beam or other system or structure to which the subject 235A may be mounted or otherwise coupled. In such embodiments, the mount 230A may be configured to maintain the subject 235A in a still, immobilized condition within the fields of view of one or more of the imaging devices 240-1, 240-2. In other embodiments, the mount 230A may be a motorized system or structure that is configured to place the subject 235A in a specific position or orientation within the fields of view of one or more of the imaging devices 240-1, 240-2, or in motion (e.g., linear or rotational) within the fields of view of one or more of the imaging devices 240-1, 240-2.

The subject 235A may be any object for which an inspection for surface flaws is desired. In some embodiments, the subject 235A may be a propeller intended for use on one or more aerial vehicles. Such a propeller may have any number of blades of any length, width, rake, pitch angle or the like. Additionally, the subject 235A may be made of any substance or material. For example, the subject 235A may be formed from any type or form of plastics (e.g., thermosetting plastics such as epoxy or phenolic resins, polyurethanes or polyesters, as well as polyethylenes, polypropylenes or polyvinyl chlorides), wood (e.g., woods with sufficient strength properties such as ash), metals (e.g., lightweight metals such as aluminum, or metals of heavier weights including alloys of steel), composites or any other combinations of materials. In some embodiments, the subject 235A may be formed of one or more lightweight materials including but not limited to carbon fiber, graphite, machined aluminum, titanium, fiberglass, wood or plastic. The sizes, shapes, types, forms or functions of the subjects 235A that may be inspected within the imaging system 210 are not limited.

The imaging devices 240-1, 240-2 may be any form of optical recording device that may be used to photograph or otherwise record imaging data of the subject 235A within the imaging system 210, or for any other purpose. The imaging devices 240-1, 240-2 may include one or more sensors, memory or storage components and processors, and such sensors, memory components or processors may further include one or more photosensitive surfaces, filters, chips, electrodes, clocks, boards, timers or any other relevant features (not shown). Such imaging devices 240-1, 240-2 may capture imaging data in the form of one or more still or moving images of any kind or form, as well as any relevant audio signals or other information, within one or more designated locations within the imaging system 210, and may be connected to the servers 212, the processors 214 and/or the data stores 216 or with one another by way of a wired or wireless connection that may be dedicated or comprise all or part of an internal network (not shown). Additionally, the imaging devices 240-1, 240-2 may be adapted or otherwise configured to communicate with the data processing system 270, or to access one or more other computer devices by way of the network 280.

Moreover, the imaging devices 240-1, 240-2 may also include manual or automatic features for modifying a respective position, field of view or orientation. For example, a digital camera may be configured in a fixed position, or with a fixed focal length (e.g., fixed-focus lenses) or angular orientation. Alternatively, the imaging devices 240-1, 240-2 may include one or more actuated or motorized features for adjusting a position of the imaging devices 240-1, 240-2, or for adjusting either the focal length (e.g., zooming the imaging devices 240-1, 240-2) or the angular orientation (e.g., a roll angle, a pitch angle or a yaw angle), by causing a change in the distance between the sensor and the lens (e.g., optical zoom lenses or digital zoom lenses), a change in the location of the imaging devices 240-1, 240-2, or a change in one or more of the angles defining the angular orientation.

For example, the imaging devices 240-1, 240-2 may be hard-mounted to a support or mounting that maintains the device in a fixed configuration or angle with respect to one, two or three axes. Alternatively, however, the imaging devices 240-1, 240-2 may be provided with one or more motors and/or controllers for manually or automatically operating one or more of the components, or for reorienting a position, axis or direction of the imaging devices 240-1, 240-2, i.e., by moving, panning or tilting the imaging devices 240-1, 240-2. Panning the imaging devices 240-1, 240-2 may cause a rotation within a horizontal plane or about a vertical axis (e.g., a yaw angle), while tilting the imaging devices 240-1, 240-2 may cause a rotation within a vertical plane or about a horizontal axis (e.g., a pitch angle). Additionally, the imaging devices 240-1, 240-2 may be rolled, or rotated about its axis of rotation (e.g., a roll angle), and within a plane that is perpendicular to the axis of rotation and substantially parallel to a field of view of the imaging devices 240-1, 240-2. The imaging devices 240-1, 240-2 may also be provided on a vehicle enabled to pass within an operating range of the imaging system 210.

The imaging devices 240-1, 240-2 may also digitally or electronically adjust an image identified in a field of view, subject to one or more physical and operational constraints. For example, the imaging devices 240-1, 240-2 may virtually stretch or condense the pixels of an image in order to focus or broaden the field of view of the imaging devices 240-1, 240-2, and also translate one or more portions of images within the field of view. Imaging devices having optically adjustable focal lengths or axes of orientation are commonly referred to as pan-tilt-zoom (or "PTZ") imaging devices, while imaging devices having digitally or electronically adjustable zooming or translating features are commonly referred to as electronic PTZ (or "ePTZ") imaging devices.

The light sources 250-1, 250-2 may be any number of flashes or lights configured to project light of any color, frequency, intensity or wavelength onto one or more surfaces of the subject 235A. In some embodiments, the light sources 250-1, 250-2 may be formed from one or more discrete lights or other addressable illuminators that are arranged in a planar configuration of any density. For example, the lights or illuminators may include any number of incandescent bulbs, fluorescent bulbs (including but not limited to compact fluorescent lights, or "CFL"), light-emitting diodes (or "LED"), studio strobe lights, or any other type or form of lights or light sources. The number and arrangement of the lights or illuminators within the light sources 250-1, 250-2 may be selected on any basis. For example, the light sources 250-1, 250-2 may include a grid or other arrangement having ten, twenty, one hundred or more lights or illuminators on either side. Additionally, the light sources 250-1, 250-2 or the discrete lights or illuminators thereof may be selectively operated, e.g., by the control system 220, in order to project light of any color, frequency or wavelength in one or more directions onto the subject 235A.

In some embodiments, the light sources 250-1, 250-2 may be specifically mounted, aligned or positioned with respect to the mount 230A and/or the subject 235A in order to ensure that surfaces of the subject 235A are properly illuminated and that specular reflections from such surfaces are minimized. For example, where the subject 235A is a propeller, such as is shown in FIG. 1A, or any other subject having one or more substantially flat surfaces, the light sources 250-1, 250-2 may be configured to project light upon surfaces of the blades of the propeller at nearly right angles of incidence, or at angles of incidence that are greater than forty-five degrees (45°), or greater than sixty degrees (60°), rather than from approximately angles of incidence that are approximately zero degrees (0°), to minimize not only the effects of specular reflections within the fields of view of the imaging devices 240-1, 240-2, but also the effects of shadowing.

Although the imaging system 210 of FIG. 2A includes two boxes corresponding to imaging devices 240-1, 240-2 and two boxes corresponding to light sources 250-1, 250-2, those of ordinary skill in the pertinent arts will recognize that any number or type of imaging devices or light sources may be provided at the imaging system 210 in accordance with the present disclosure. Moreover, in addition to the imaging devices 240-1, 240-2 and the light sources 250-1, 250-2, the imaging system 210 may further include any other types or forms of sensors that may be used to capture information or data regarding the subject 235A, including but not limited to one or more environmental sensors, operational sensors, or the like. For example, the imaging system 210 may include one or more wind speed sensors (e.g., pitot tubes and/or anemometers), temperature or heat sensors (e.g., thermometers), accelerometers, gyroscopes, barometers, air monitoring sensors, infrared sensors or acoustic sensors (e.g., microphones, piezoelectric sensors, vibration sensors having one or more transducers) for determining environmental and/or operational conditions of the subject 235A during testing operations.

The data processing system 270 includes one or more physical or virtual computer servers 272 having a plurality of processors 274 provided for any specific or general purpose, and at least one data store (e.g., one or more databases) 276 associated therewith. For example, the data processing system 270 of FIGS. 2A and 2B may be independently provided for the exclusive purpose of receiving, analyzing or storing imaging data and/or associated audio signals or other data captured by the one or more imaging devices 240-1, 240-2 or, alternatively, provided in connection with one or more physical or virtual services that are configured to receive, analyze or store such data, or perform any other functions. The servers 212 may be connected to or otherwise communicate with the processors 274 and the data stores 276. The data stores 276 may store any type of information or data, including but not limited to acoustic signals, information or data relating to acoustic signals, or information or data regarding environmental conditions, operational characteristics, or positions, for any purpose. The servers 272 and/or the computer processors 274 may also connect to or otherwise communicate with the network 280, as indicated by line 278, through the sending and receiving of digital data. For example, the data processing system 270 may include any facilities, stations or locations having the ability or capacity to receive and store information or data, such as media files, in one or more data stores, e.g., media files received from the imaging system 210, or from one or more other external computer systems (not shown) via the network 280. In some embodiments, the data processing system 270 may be provided in a physical location. In other such embodiments, the data processing system 270 may be provided in one or more alternate or virtual locations, e.g., in a "cloud"-based environment.

The network 280 may be any wired network, wireless network, or combination thereof, and may comprise the Internet in whole or in part. In addition, the network 280 may be a personal area network, local area network, wide area network, cable network, satellite network, cellular telephone network, or combination thereof. The network 280 may also be a publicly accessible network of linked networks, possibly operated by various distinct parties, such as the Internet. In some embodiments, the network 280 may be a private or semi-private network, such as a corporate or university intranet. The network 280 may include one or more wireless networks, such as a Global System for Mobile Communications (GSM) network, a Code Division Multiple Access (CDMA) network, a Long-Term Evolution (LTE) network, or some other type of wireless network. Protocols and components for communicating via the Internet or any of the other aforementioned types of communication networks are well known to those skilled in the art of computer communications and thus, need not be described in more detail herein.

Although the block diagram of the system 200 shown in FIG. 2A includes a subject 235A mounted or otherwise coupled to a mount 230A, those of ordinary skill in the pertinent arts will recognize that one or more components of the imaging system 210 may be utilized in connection with any type or form of subject that is provided in association with the imaging system 210 by any type or form of mount. For example, as is shown in FIG. 2B, the imaging system 210 may be used to capture imaging data regarding one or more images of components of an aerial vehicle 245 having one or more motors 230B coupled to one or more propellers 235B. For example, referring again to FIG. 1A, one or more aspects of an aerial vehicle, e.g., frames, propulsion motors, propellers, or control surfaces (e.g., rudders, elevators, stabilizers, spoilers, ailerons, flaps or slats), may be inserted between the imaging devices 140-1, 140-2, and illuminated using the light sources 150-1, 150-2. Imaging data may be captured from the aerial vehicle 245 with such aspects in stationary or in motion, e.g., by operating the propulsion motors and/or propellers at various speeds, or by operating the control surfaces at various degrees of deflection. Alternatively, images of any other subject may be captured using the imaging system 210.

The computers, servers, devices and the like described herein have the necessary electronics, software, memory, storage, databases, firmware, logic/state machines, microprocessors, communication links, displays or other visual or audio user interfaces, printing devices, and any other input/output interfaces to provide any of the functions or services described herein and/or achieve the results described herein. Also, those of ordinary skill in the pertinent art will recognize that users of such computers, servers, devices and the like may operate a keyboard, keypad, mouse, stylus, touch screen, or other device (not shown) or method to interact with the computers, servers, devices and the like, or to "select" an item, link, node, hub or any other aspect of the present disclosure.

The imaging system 210 or the data processing system 270 may use any web-enabled or Internet applications or features, or any other client-server applications or features including E-mail or other messaging techniques, to connect to the network 280, or to communicate with one another, such as through short or multimedia messaging service (SMS or MMS) text messages. For example, the imaging system 210 may be adapted to transmit information or data in the form of synchronous or asynchronous messages to the data processing system 270 or to any other computer device in real time or in near-real time, or in one or more offline processes, via the network 280. Those of ordinary skill in the pertinent art would recognize that the aerial vehicle 210 or the data processing system 270 may operate, include or be associated with any of a number of computing devices that are capable of communicating over the network, including but not limited to set-top boxes, personal digital assistants, digital media players, web pads, laptop computers, desktop computers, electronic book readers, and the like. The protocols and components for providing communication between such devices are well known to those skilled in the art of computer communications and need not be described in more detail herein.

The data and/or computer executable instructions, programs, firmware, software and the like (also referred to herein as "computer executable" components) described herein may be stored on a computer-readable medium that is within or accessible by computers or computer components such as the processor 214 or the processor 274, or any other computers or control systems utilized by the imaging system 210 or the data processing system 270, and having sequences of instructions which, when executed by a processor (e.g., a central processing unit, or "CPU"), cause the processor to perform all or a portion of the functions, services and/or methods described herein. Such computer executable instructions, programs, software, and the like may be loaded into the memory of one or more computers using a drive mechanism associated with the computer readable medium, such as a floppy drive, CD-ROM drive, DVD-ROM drive, network interface, or the like, or via external connections.

Some embodiments of the systems and methods of the present disclosure may also be provided as a computer-executable program product including a non-transitory machine-readable storage medium having stored thereon instructions (in compressed or uncompressed form) that may be used to program a computer (or other electronic device) to perform processes or methods described herein. The machine-readable storage media of the present disclosure may include, but is not limited to, hard drives, floppy diskettes, optical disks, CD-ROMs, DVDs, ROMs, RAMs, erasable programmable ROMs ("EPROM"), electrically erasable programmable ROMs ("EEPROM"), flash memory, magnetic or optical cards, solid-state memory devices, or other types of media/machine-readable medium that may be suitable for storing electronic instructions. Further, embodiments may also be provided as a computer executable program product that includes a transitory machine-readable signal (in compressed or uncompressed form). Examples of machine-readable signals, whether modulated using a carrier or not, may include, but are not limited to, signals that a computer system or machine hosting or running a computer program can be configured to access, or including signals that may be downloaded through the Internet or other networks.

Figure 3A:
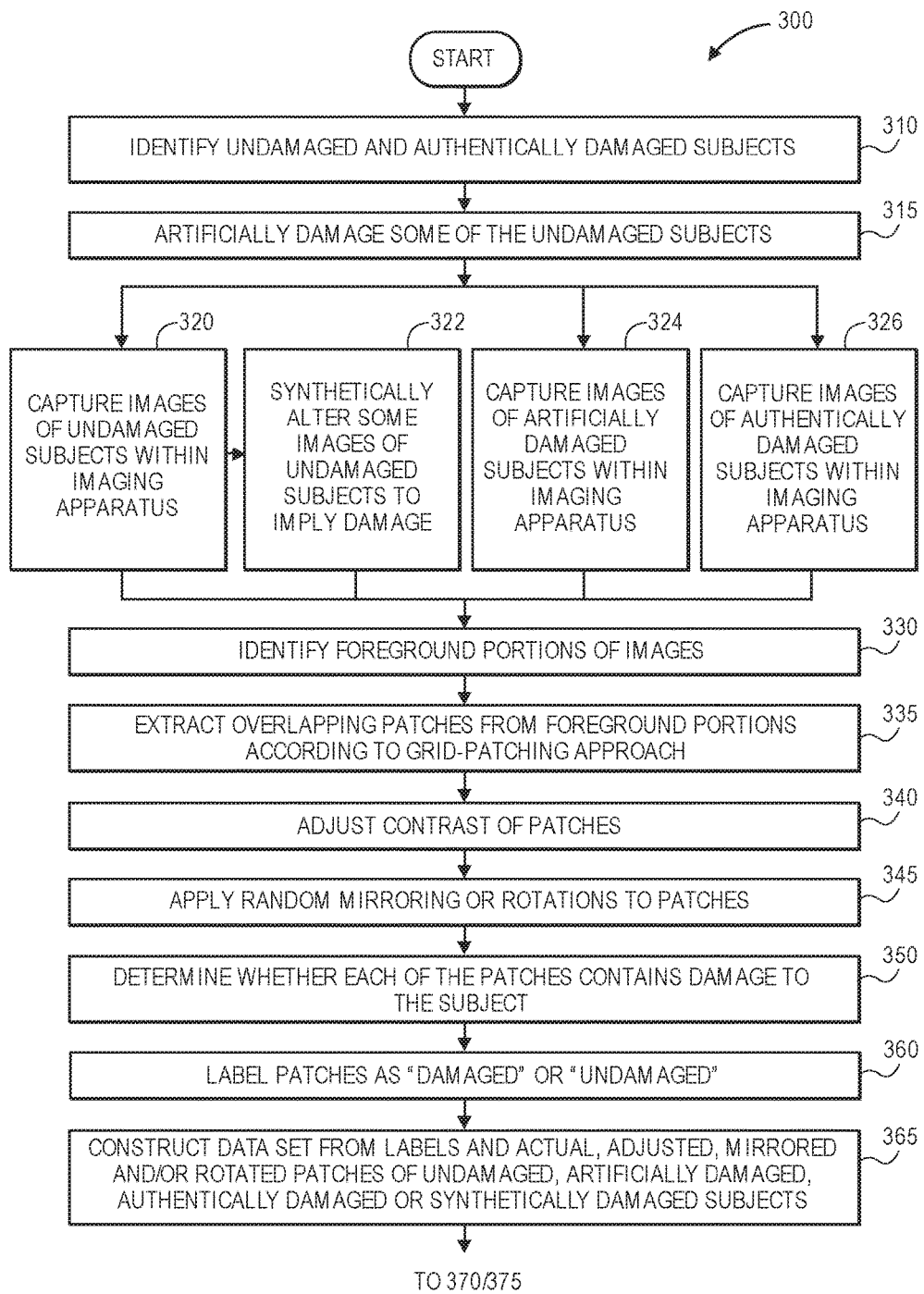
FIGS. 3A and 3B are a flow chart of one process for detecting surface flaws using computer vision in accordance with embodiments of the present disclosure.
Figure 3B:
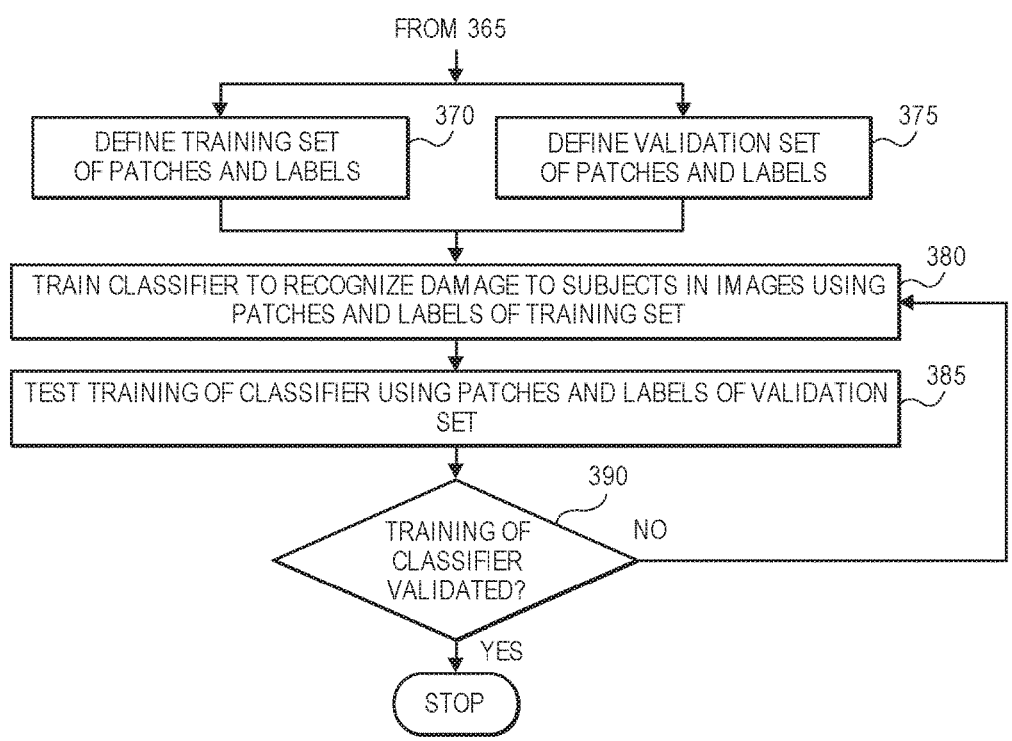

As is discussed above, a classifier such as a convolutional neural network may be trained to recognize damaged subjects using labeled images of damaged subjects and labeled images of undamaged subjects. The damaged subjects may have been damaged during operation, or artificially damaged. Alternatively, some images of undamaged subjects may be synthetically altered to indicate damage to one or more elements. Referring to FIGS. 3A and 3B, a flow chart 300 of one process for detecting surface flaws using computer vision in accordance with embodiments is shown. At box 310, undamaged and authentically damaged subjects are identified. The status of the respective undamaged and damaged subjects may be confirmed by manual and/or visual inspections by humans, or by any other manual or artificial techniques.

At box 315, some of the undamaged subjects are artificially damaged. For example, the undamaged subjects may be struck with a hammer, a mallet or another like tool, or physically manipulated using a drill, an awl, a punch, a knife or a saw that may puncture or wear away one or more surfaces of such subjects. Any manual or automatic system or device for physically altering an undamaged subject may be utilized to impart artificial damage upon an undamaged article in accordance with the present disclosure.

Subsequently, images are captured of the damaged and undamaged subjects using an imaging apparatus having one or more features or components in common with the imaging system 110 of FIG. 1A, or another imaging apparatus. Preferably, the images are captured with sufficient resolution and depth of field to ensure that surface flaws on the subjects are visible even when fields of view of the imaging devices are sufficiently large, i.e., to capture the entire subjects within a single image. At box 320, images of the undamaged subjects are captured within an imaging apparatus. For example, referring again to FIG. 1A, an imaging apparatus may include one or more imaging devices and one or more light sources aligned substantially parallel to one or more surfaces of the subjects, and substantially transverse (or perpendicular) to the axes of orientation of the imaging devices, or from different perspectives with respect to the subjects, thereby minimizing the amount of specular reflections or shadowing that may be visible within images captured using the imaging devices. The light sources may include a plurality of individual lights or illuminators distributed in a planar or other configuration, thereby ensuring that the total amount of light cast upon the subjects is sufficient to illuminate the entire subject, while minimizing the specular reflections caused by any one of the lights or illuminators.

At box 322, some of the images of the undamaged subjects are synthetically altered to imply that such subjects are damaged using one or more image processing tools. For example, one or more image processing applications or systems may be used to alter such images to include visual representations of surface flaws (e.g., microfractures, cracks, loosened or broken fasteners, corrosions, fatigue, or evidence of other physical manifestations of stress or strain). In some embodiments, a generative adversarial network having an architecture featuring one or more networks may be utilized to alter the images to include surface flaws and/or to refine the appearance of the synthesized surface flaws therein. For example, in some embodiments, a generative adversarial network may include a refiner network for enhancing the appearance of the synthesized images, and a discriminator network for distinguishing between synthetic images and real images. In some embodiments, the refiner network may include two or more convolutional layers for convolving a three-channel (e.g., RGB) input image through one or more residual blocks, resulting in an output product that corresponds to a refined synthetic image. In some embodiments, the discriminator network may include two or more (e.g., as many as five) convolutional layers, as well as any number of other layers (such as pooling layers). Locations of the synthetic damage within the altered images may be marked or identified according to one or more annotation processes, or in any other manner, and such locations may be stored in a record maintained in association with the altered image or as metadata within the altered image file. For example, one or more bounding boxes may be manually or automatically applied to such locations either manually or automatically using one or more image processing applications. Such bounding boxes may defined by boundaries or barriers of any shape (e.g., traditional "boxes" in the form of squares or rectangles, as well as curved shapes such as circles, ellipses or ovals, or polygons such as triangles, pentagons or shapes having any number of straight sides), and may occupy any number of pixels within such images. Additionally, the boundaries or barriers of such bounding boxes may have thicknesses of any number of pixels. The bounding boxes may be defined as the synthetic damage is generated or shortly thereafter, or at any later time.

At box 324, images of the artificially damaged subjects are captured within the imaging apparatus, and at box 326, images of the authentically damaged subjects are captured within the imaging apparatus. As is discussed above with regard to the synthetically altered images, locations of artificial or authentic damage within images may be marked or identified according to one or more annotation processes, or in any other manner, such as by manually or automatically applying one or more bounding boxes in such locations, as is discussed above, and such locations may be stored in a record maintained in association with the altered image or as metadata within the altered image file.

At box 330, foreground portions of the images captured at box 320, box 324 and box 326, and the images synthetically altered at box 322, are identified. In some embodiments, the foreground portions of the images may be identified using any type or form of edge detection algorithm or technique. For example, the foreground portions may be identified through adaptive thresholding, e.g., using Otsu binarization, or by any other technique. At box 335, a plurality of overlapping patches are extracted from the foreground portions of the images according to a grid-patching approach, e.g., at a predetermined stride. For example, in some embodiments, a grid of overlapping patches having predetermined dimensions, such as four hundred pixels by four hundred pixels in size, may be extracted from the foreground portions of the images at a predetermined stride, such as approximately three hundred pixels.

At box 340, the contrast of one or more of the patches is optionally adjusted, as necessary, in order to increase the likelihood that damages depicted within the patch are visible to the system. The adjustment in contrast is optional, not mandatory, and may be applied where a portion of the subject depicted within the patch lacks sufficient contrast to cause flaws to appear in a distinct manner with respect to the material texture. At box 345, one or more of the patches are duplicated and optionally mirrored, on a random basis, and/or subjected to rotations. For example, additional patches may be derived from the patches extracted at box 335, such as by mirroring and rotating patches by any angle or extent, e.g., by ninety degrees (90°). The mirroring and/or rotation of the patches is also optional, not mandatory, and may be performed to expand a number of available patches (e.g., patches depicting authentic, artificial and/or synthetic damage, and also patches that do not depict damage), particularly where a number of available damaged or undamaged subjects for generating a data set is low.

At box 350, whether each of the patches depicts damage to a subject is determined. For example, the patches may be identified as damaged or undamaged based on the images from which such patches originated, e.g., whether the patches were extracted from an image captured from an authentically or artificially damaged subject, or an undamaged subject, or whether the patches depict portions of an undamaged subject and have been synthetically altered to include visual representations of damage accordingly. Whether a portion of a given patch depicts, or does not depict, damage may be identified by one or more human operators, e.g., by annotation, or according to any algorithm or technique. In some embodiments, a patch may be determined to depict damage where an outer boundary or barrier of a patch intersects a boundary or barrier of a bounding box applied to a location of an image, as is discussed above with regard to box 322, box 324 or box 326. In some embodiments, where the patches have a predetermined size such as four hundred pixels by four hundred pixels, whether a central subset or region of the patch comprising approximately three hundred pixels by three hundred pixels depicts damage to a subject may be determined. The central subset or region may have any buffer or offset with respect to a boundary of the patch. If damage to a subject is recognized within the central subset or region of the patch, the patch may be deemed to depict damage to the subject. At box 360, the patches that have been identified as depicting damage to subjects, or as not depicting damage to subjects, are labeled as "damaged" or "undamaged," accordingly.

At box 365, a data set is constructed from the labels and the actual, adjusted, mirrored and/or rotated patches depicting subjects, including the undamaged subjects, the artificially damaged subjects and the authentically damaged subjects, as well as the patches depicting undamaged subjects that have been synthetically altered to include visual representations of damages to the subjects. In some embodiments, the data set may be constructed from the patches extracted from the foreground portions of the images at box 335. In some other embodiments, patches that have been subjected to contrast adjustment, mirroring and/or rotation may also be used to construct the data set. Alternatively, the data set may be constructed from entire images that have been labeled as "damaged" or "undamaged'," accordingly.

At box 370, a training set of patches and labels is defined from the data set. For example, the training set may comprise a substantially large portion of the patches and corresponding labels of the data set. In some embodiments, the training set may comprise approximately eighty-five percent (85%), or more, of the patches and labels of the data set. At box 375, a validation set of patches and labels is defined from the data set. For example, the validation set may comprise a balance of the patches and the corresponding labels in the data set that are not included in the training set.

At box 380, the classifier is trained to recognize damage to subjects in images using the patches and the corresponding labels of the training set. For example, a patch may be provided to a classifier, such as a convolutional neural network, as an input, and an output received from the classifier may be compared to the label corresponding to the patch. In some embodiments, the output received from the classifier may represent a probability (e.g., a number between 0 and 1, or a number according to any scale), indicative of whether the patch does or does not depict damage. The output may thus be compared to the label corresponding to the patch to determine whether the classifier is sufficiently trained to recognize damage (e.g., surface flaws) within images of subjects.

For example, in some embodiments, a very deep convolutional network configured for large-scale image recognition with bilinear pooling may be trained for use in detecting and classifying damage to subjects. Bilinear pooling may be used to produce a robust descriptor of the image by combining sets of extracted features at each location in an image, and using a pooling operation, e.g., summing, to determine such descriptors. In some embodiments, the convolutional neural network may be a symmetrical bilinear convolutional neural network. An output of the symmetrical bilinear convolutional neural network may be extracted, and batch normalization may be applied to the output. Subsequently, a bilinear pooling operation (e.g., with summing) may be performed on the normalized output, with dropout applied. A fully connected softmax function layer may then predict probabilities for each of a pair of labels or classifications, viz., "damaged" or "undamaged." Alternatively, in some embodiments, a compact bilinear layer may also be utilized.

At box 385, the training of the classifier is tested using the patches and the labels of the validation set. For example, to determine the extent to which the classifier has been properly trained, an image of the validation set may be provided to the classifier as an input, and a label corresponding to the image of the validation set may be compared to an output received from the classifier. The testing of the classifier may occur at various times or intervals with respect to the number of patches and labels provided to the classifier. For example, the classifier may be tested after every ten, one hundred or any other number of patches of the training set have been provided to train the classifier as inputs.

At box 390, whether the classifier is properly trained is determined based on the testing using the validation set. For example, whether the output received from the classifier in response to an input from the validation set is sufficiently close to the label, e.g., where the output is a numerical value that is within a predetermined threshold of a value deemed satisfactory for the label, or where the output is a binary value that corresponds to the label, may be determined. If the classifier is not satisfactorily trained, then the process returns to box 380, where the classifier is again trained to recognize damage to subjects in images. Any number of iterations may be required in order to properly train the classifier using the patches and labels of the training set. If the training of the classifier is validated, however, then the process ends.

Figure 4A:
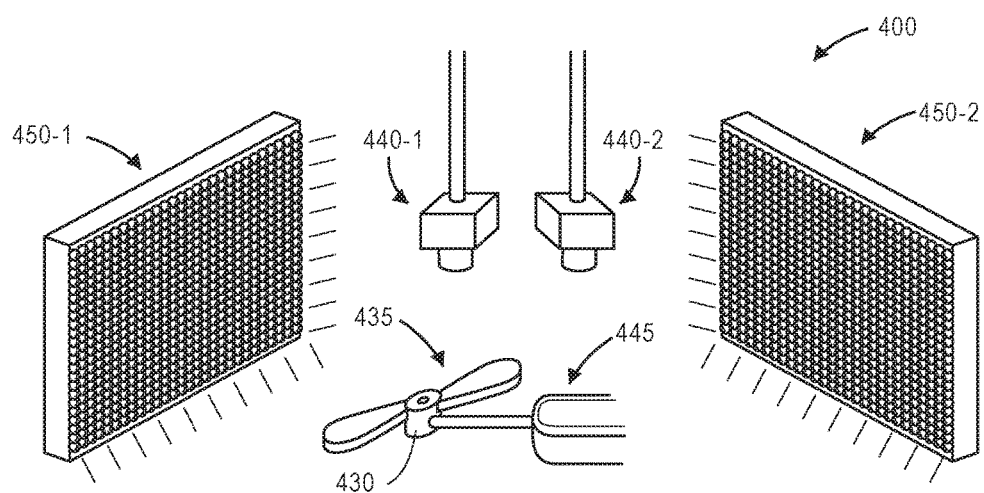
FIGS. 4A and 4B are views of aspects of one system for detecting surface flaws using computer vision in accordance with embodiments of the present disclosure.
Figure 4B:
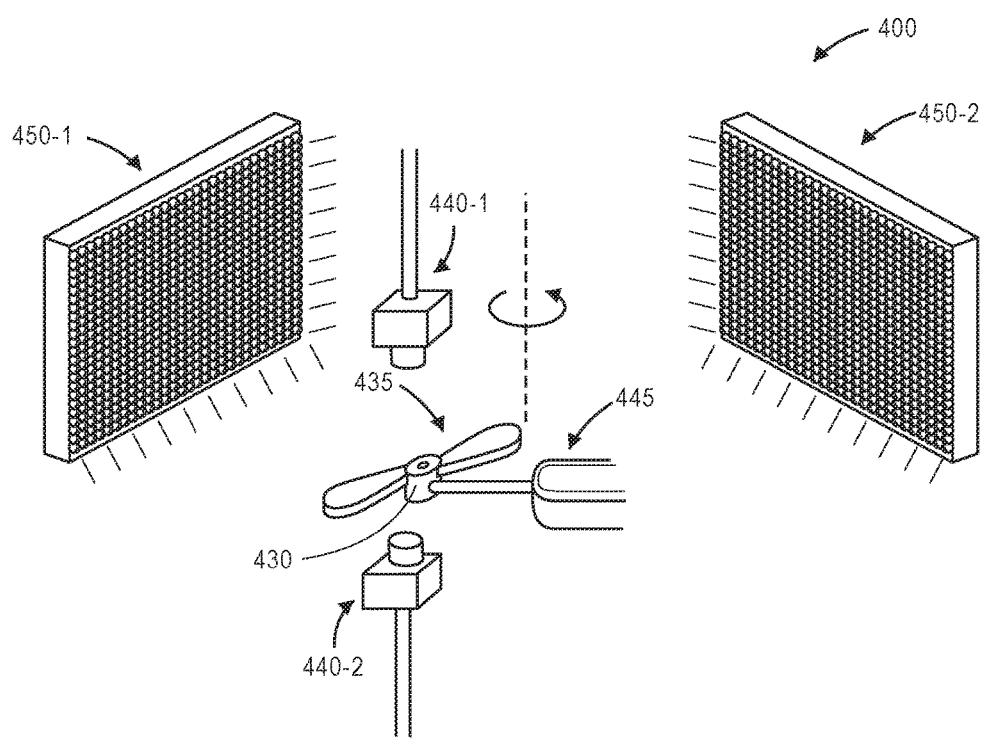

As is discussed above, images for training a classifier to recognize damages such as surface flaws in subjects, or images of subjects that are to be inspected using the trained classifier, may be captured using imaging systems having one or more imaging devices that are configured to illuminate the subjects from one or more directions. Referring to FIGS. 4A and 4B, views of aspects of one system for detecting flaws using computer vision in accordance with embodiments of the present disclosure are shown. Except where otherwise noted, reference numerals preceded by the number "4" shown in FIG. 4A or 4B indicate components or features that are similar to components or features having reference numerals preceded by the number "2" shown in FIG. 2A or 2B or by the number "1" shown in FIG. 1A or 1B.

As is shown in FIG. 4A, a system 400 includes a pair of imaging devices 440-1, 440-2, an aerial vehicle 445 and a pair of light sources 450-1, 450-2. The aerial vehicle 445 includes a motor 430 and a propeller 435 rotatably coupled to the motor 430. The motor 430 and the propeller 435 are provided within the fields of view of the imaging devices 440-1, 440-2, such that surfaces of the propeller 435 are substantially perpendicular to axes of orientation of the imaging devices 440-1, 440-2. Thus, the imaging devices 440-1, 440-2 may be used to capture imaging data from one side or face of the propeller 435, as the propeller 435 is fixed in any angular rotation about an axis defined by the motor 430, or while the propeller 435 is in motion.

Additionally, the light sources 450-1, 450-2 are directionally diffuse sources of light that illuminate the propeller 435, and enable surface flaws (if any) within the propeller 435 to appear within imaging data captured from the subject, while also minimizing or avoiding specular reflections. For example, the light sources 450-1, 450-2 may include a plurality of lights or illuminators that are distributed in association with a substantially planar surface, thereby minimizing the amount of light originating from any single point, and reducing the extent of any reflections thereon. Additionally, the light sources 450-1, 450-2 are aligned such that their respective planar surfaces are substantially perpendicular to surfaces of the propeller 435, or provided at comparatively large angles of incidence with respect to the surfaces of the propeller 435. For example, in some embodiments, the angles of incidence of light onto the propeller 435 from the light sources 450-1, 450-2 are approximately forty-five degrees (45°), or greater than forty-five degrees (45°). In some other embodiments, the angles of incidence of light onto the propeller 435 from the light sources 450-1, 450-2 are approximately sixty degrees (60°), or greater than sixty degrees (60°). In some other embodiments, the angles of incidence of light onto the propeller 435 from the light sources 450-1, 450-2 are nearly ninety degrees (90°). The alignment of the light sources 450-1, 450-2 as shown in FIG. 4A further minimizes the extent of any specular reflections on the surfaces of the propeller 435.

In some embodiments, the system 400 may be used to capture imaging data from a single side of the propeller 435, such as is shown in FIG. 4A, or from both sides of the propeller 435. As is shown in FIG. 4B, the propeller 435 is shown as being positioned within the fields of view of the imaging devices 440-1, 440-2. In particular, the imaging device 440-1 is shown as being mounted above the propeller 435, and configured to capture imaging data including one side or face of the propeller 435, while the imaging device 440-2 is shown as being mounted below the propeller 435, and configured to capture imaging data including an opposite side or face of the propeller 435. The orientation of the respective imaging devices 440-1, 440-2 shown in FIG. 4B enables imaging data to be captured from both sides or faces of the propeller 435 simultaneously, and with the propeller 435 in a fixed or variable orientation. In some embodiments, only a single imaging device need be used, and the imaging device may be used to capture images from a first side of the propeller 435 before being inverted and used to capture images from a second side of the propeller 435. In other embodiments, the propeller 435 may be coupled to a fixed or rotating mount, other than the aerial vehicle 445 or the motor 430, and imaging data may be captured from the propeller 435 using either or both of the imaging devices 440-1, 440-2.

Figure 5:
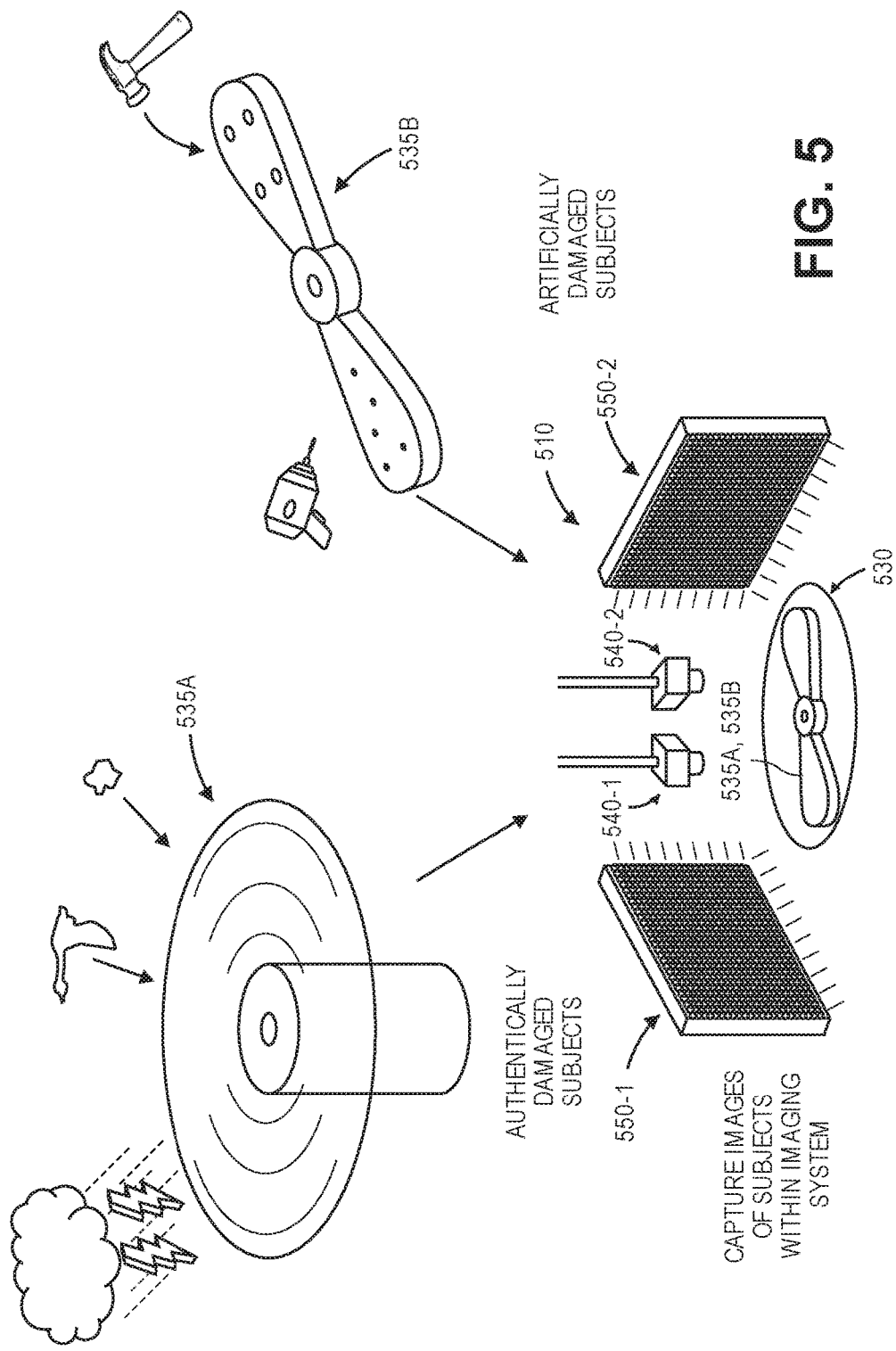
FIG. 5 is a view of aspects of one system for detecting surface flaws using computer vision in accordance with embodiments of the present disclosure.

As is discussed above, a convolutional neural network or other classifier may be trained to recognize surface flaws in subjects using labeled images of undamaged subjects, as well as labeled images of damaged subjects, including both authentically damaged subjects (e.g., subjects damaged in the ordinary course of operations) and artificially damaged subjects. Referring to FIG. 5, a view of aspects of one system for detecting flaws using computer vision in accordance with embodiments of the present disclosure is shown. Except where otherwise noted, reference numerals preceded by the number "5" shown in FIG. 5 indicate components or features that are similar to components or features having reference numerals preceded by the number "4" shown in FIG. 4A or 4B, by the number "2" shown in FIG. 2A or 2B or by the number "1" shown in FIG. 1A or 1B.

As is shown in FIG. 5, an imaging system 510 includes a mount 530, a pair of imaging devices 540-1, 540-2 and a pair of light sources 550-1, 550-2. The imaging system 510 may be used to capture images of authentically damaged subjects 535A, e.g., propellers that are damaged by weather, biologics, stones or other debris, or any other matter during operation, as well as artificially damaged subjects 535B, e.g., propellers that are manually or automatically damaged using one or more tools or other systems. Either of the subjects 535A, 535B may be placed on the mount 530 within the fields of view of the imaging devices 540-1, 540-2 and imaging data may be captured accordingly. Alternatively, the imaging system 510 may include a fixed or rotating mount with one of the imaging devices 540-1 oriented toward a first side or face of either of the subjects 535A, 535B (e.g., above the subjects 535A, 535B), and another of the imaging devices 540-2 oriented toward a second side or face of either of the subjects 535A, 535B (e.g., below the subjects 535A, 535B), such that imaging data may be captured from either both of the sides or faces of the subjects 535A, 535B simultaneously.

In some embodiments, patches may be extracted from images captured of the subjects 535A, 535B, labeled, e.g. by one or more annotation techniques, and added to a data set accordingly. Alternatively, in some other embodiments, images captured from the subjects 535A, 535B may be labeled, e.g., by one or more annotation techniques, and added to a data set accordingly. The data set may be used to define a training set of labels and patches (or images), and a validation set of labels and patches (or images). The training set and the validation set may be used to train a convolutional neural network or other classifier to recognize damages within subjects based on imaging data.

Figure 6:
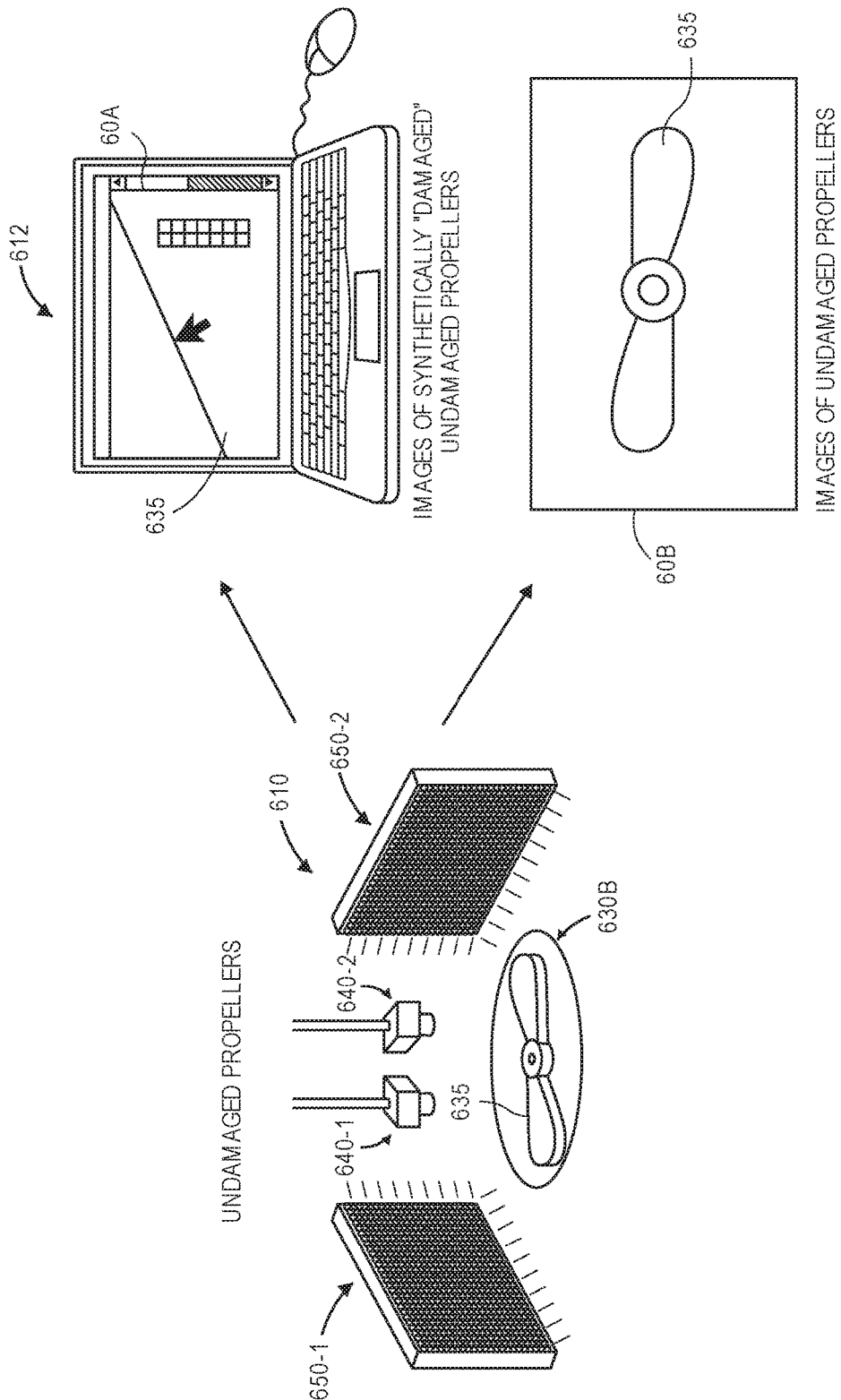
FIG. 6 is a view of aspects of one system for detecting surface flaws using computer vision in accordance with embodiments of the present disclosure.

Additionally, as is also discussed above, images may also be captured from undamaged subjects and used to train a classifier. Some of the images captured from the undamaged subjects may be further processed to simulate damage thereon, e.g., by adding visual representations to the portions of subjects depicted within the images using one or more image processing tools. Referring to FIG. 6, a view of aspects of one system for detecting flaws using computer vision in accordance with embodiments of the present disclosure is shown. Except where otherwise noted, reference numerals preceded by the number "6" shown in FIG. 6 indicate components or features that are similar to components or features having reference numerals preceded by the number "5" shown in FIG. 5, by the number "4" shown in FIG. 4A or 4B, by the number "2" shown in FIG. 2A or 2B or by the number "1" shown in FIG. 1A or 1B.

As is shown in FIG. 6, an imaging system 610 includes a mount 630B, a pair of imaging devices 640-1, 640-2 and a pair of light sources 650-1, 650-2. The imaging system 610 may be used to capture images of an undamaged subject 635 (viz., a propeller). Once the imaging devices 640-1, 640-2 have captured images 60A, 60B of the undamaged subject 635, some of the images 60A may be synthetically altered to include visual representations of damage on the subject 635. By synthetically altering the image 60A of the undamaged subject 635 to imply damage thereon, the number of damaged images in a data set may be increased without actually having to damage a subject, as creating a visual representation of damage on an image of an undamaged subject is less costly and requires less labor than artificially damaging a subject and capturing images of the object. Moreover, in some applications, artificially creating realistic-looking damage using one or more tools or procedures may be challenging, as authentic damage to a subject, such as a propeller, may occur in more subtle ways and in different scenarios.

Visual representations may be applied to images of subjects as a whole, or to discrete patches extracted from such images. In some embodiments, when a visual representation of a surface flaw or other damage is applied to an image of a subject, the image may be refined to cause the visual representation to appear more realistic. For example, a generative adversarial network having a refiner network and a discriminator network may refine synthetically altered images to make them look more realistic, e.g., using the refiner network, and also to distinguish between synthetically altered images and images of authentically damaged subjects or artificially damaged subjects.

Figure 7:
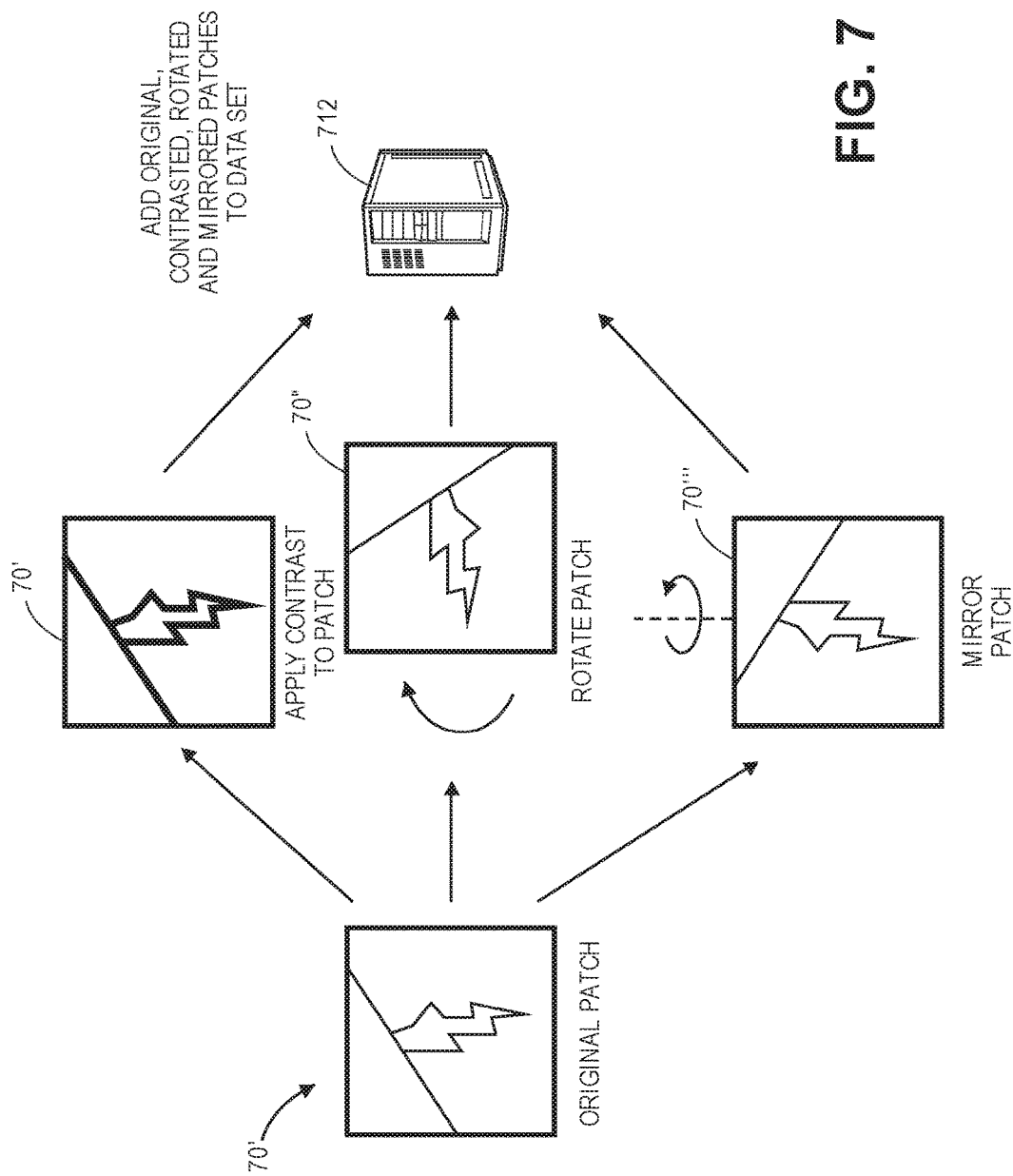
FIG. 7 is a view of aspects of one system for detecting surface flaws using computer vision in accordance with embodiments of the present disclosure.

Patches including surface flaws or other damage may be further processed prior to including such patches in a data set for training a classifier, or for validating a trained classifier. Referring to FIG. 7, a view of aspects of one system for detecting flaws using computer vision in accordance with embodiments of the present disclosure is shown. Except where otherwise noted, reference numerals preceded by the number "7" shown in FIG. 7 indicate components or features that are similar to components or features having reference numerals preceded by the number "6" shown in FIG. 6, by the number "5" shown in FIG. 5, by the number "4" shown in FIG. 4A or 4B, by the number "2" shown in FIG. 2A or 2B or by the number "1" shown in FIG. 1A or 1B.

As is shown in FIG. 7, a patch 70 depicting damage to a subject that has been extracted from an image may be subjected to further processing prior to providing the patch 70 to a data set, which may be maintained on a server 712 for the purpose of training a classifier or validating a trained classifier. For example, where the patch 70 includes an inadequate level of contrast, the exposure of the patch 70 may be adjusted to result in a patch 70' having an adequate level of contrast that enables damage depicted therein to become more clearly visible. Alternatively, the patch 70 may be randomly rotated, e.g., by ninety degrees (90°), to generate a patch 70" having surface flaws or other damage aligned in a transverse or alternate direction as compared to the surface flaws or other damage depicted in the patch 70. The patch 70 may also be mirrored, e.g., rotated by one hundred eighty degrees (180°) about an axis, to generate a patch 70''' having surface flaws or other damage aligned in a reciprocal fashion as compared to the surface flaws or other damage depicted in the patch 70.

Thus, an image or patch depicting surface flaws or other damage may be processed in any manner, thereby resulting in multiple different images or patches, and enlarging the size or number of images in a data set that may be used to train a classifier to recognize surface flaws or other damage within images, or to validate the training of such a classifier. Any of the processing techniques applied to the patch 70 shown in FIG. 7, or any other processing techniques, may be applied to images of subjects as a whole, or to patches extracted from such images, such as the patch 70, in accordance with the present disclosure. Moreover, any of the processing techniques applied to the patch 70 shown in FIG. 7, or any other processing techniques, may be applied to patches that are extracted directly from an image of a damaged or undamaged subject, or to duplicates of such patches. In this regard, a single patch may result in four different patches that may be used to populate a data set, e.g., not only the patch 70 but also the patch 70', the patch 70" and the patch 70''' shown in FIG. 7, or any other patches resulting from processing of the patch 70. Moreover, although the patch 70 is shown as depicting damage to a subject therein, any number of the processing techniques referenced in FIG. 7, or any other processing techniques, may be performed on patches that depict damage, or do not depict damage, to an underlying subject shown therein.

An image of a subject may be processed according to a patch-based classification system to determine whether specific regions of the subject include one or more surface flaws or other damage. Referring to FIGS. 8A through 8F, views of aspects of one system for detecting flaws using computer vision in accordance with embodiments of the present disclosure are shown. Except where otherwise noted, reference numerals preceded by the number "8" shown in FIGS. 8A through 8F indicate components or features that are similar to components or features having reference numerals preceded by the number "7" shown in FIG. 7, by the number "6" shown in FIG. 6, by the number "5" shown in FIG. 5, by the number "4" shown in FIG. 4A or 4B, by the number "2" shown in FIG. 2A or 2B or by the number "1" shown in FIG. 1A or 1B.

Figure 8A:
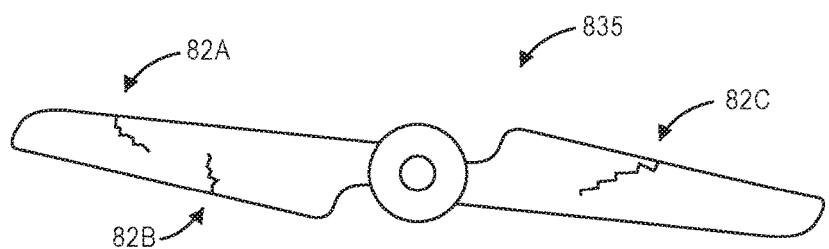

As is shown in FIG. 8A, a subject 835 (e.g., a propeller) having one or more surface flaws 82A, 82B, 82C may be evaluated using one or more of the systems and methods of the present disclosure. For example, one or more of the surface flaws 82A, 82B, 82C may be microfractures, cracks, loosened or broken faces, corrosions, fatigue, or evidence of other physical manifestations of stress or strain.

Figure 8B:
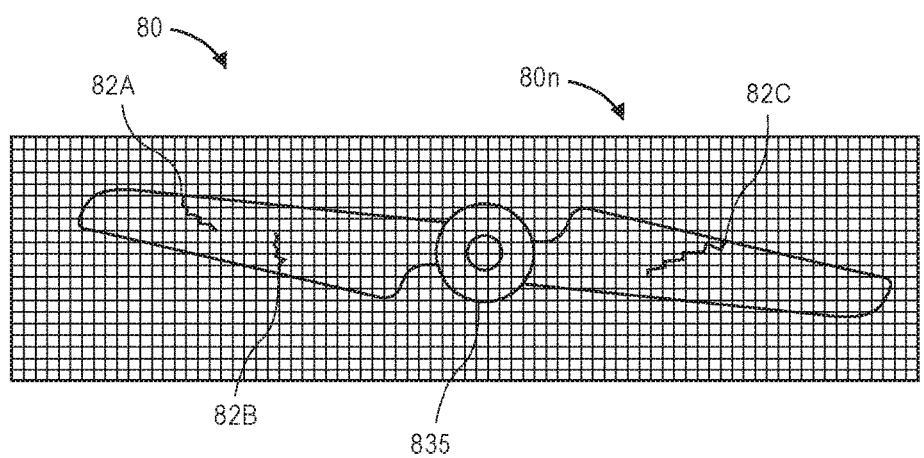

As is shown in FIG. 8B, an image 80 may be captured from the subject 835 and processed to extract a plurality of patches 80$n$ therefrom. The patches 80$n$ may have any size, and may be extracted in an overlapping fashion to ensure that each of the pixels corresponding to the subject 835 within the image 80 is represented in at least one of the patches 80$n$. The patches 80$n$ may have any dimensions, and may overlap to any extent. As is shown in FIG. 8C, the patches 80$n$ corresponding to the subject 835, e.g., patches including foreground pixels within the image 80, may be identified and processed to determine whether any of such patches depicts surface flaws or other damages therein. In some embodiments, the foreground and background pixels within the image 80 may be identified after the patches 80$n$ have been extracted from the image 80. In some other embodiments, however, the foreground and background pixels within the image 80 may be identified prior to extracting the patches 80$n$ from the image. For example, background pixels of the image 80 may be identified by adaptive thresholding, such as by Otsu binarization, and patches may be extracted from pixels other than the background pixels (e.g., foreground pixels) within the image 80.

The patches 80$n$ may overlap to any extent. For example, as is shown in FIG. 8D, patches 80-$i$, 80-($i$+1), 80-($i$+2) may be squares having dimensions of w by w, and centers $C_i$, $C_{i+1}$, $C_{i+2}$ of the respective patches 80-$i$, 80-($i$+1), 80-($i$+2) may be separated by a stride S. In some embodiments, each of the patches may be squares having dimensions w of four hundred pixels by four hundred pixels, and may be separated by strides S of three hundred pixels, such that pairs of overlapping patches have at least one hundred pixels in common, in a given direction. Although the patches 80-$i$, 80-($i$+1), 80-($i$+2) are shown in a horizontal arrangement, patches may be separated in a similar fashion vertically. Additionally, although the patches are shown as squares, the patches 80-$i$, 80-($i$+1), 80-($i$+2) may have any shape in accordance with the present disclosure (e.g., squares, rectangles, circles, ellipses, ovals, triangles, pentagons or any other shapes).

Figure 8E:
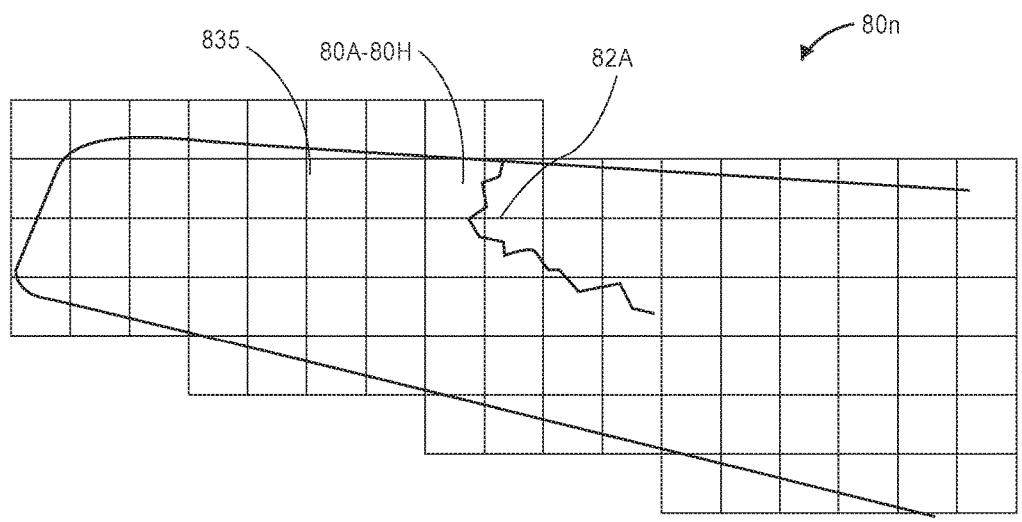
Figure 8F:
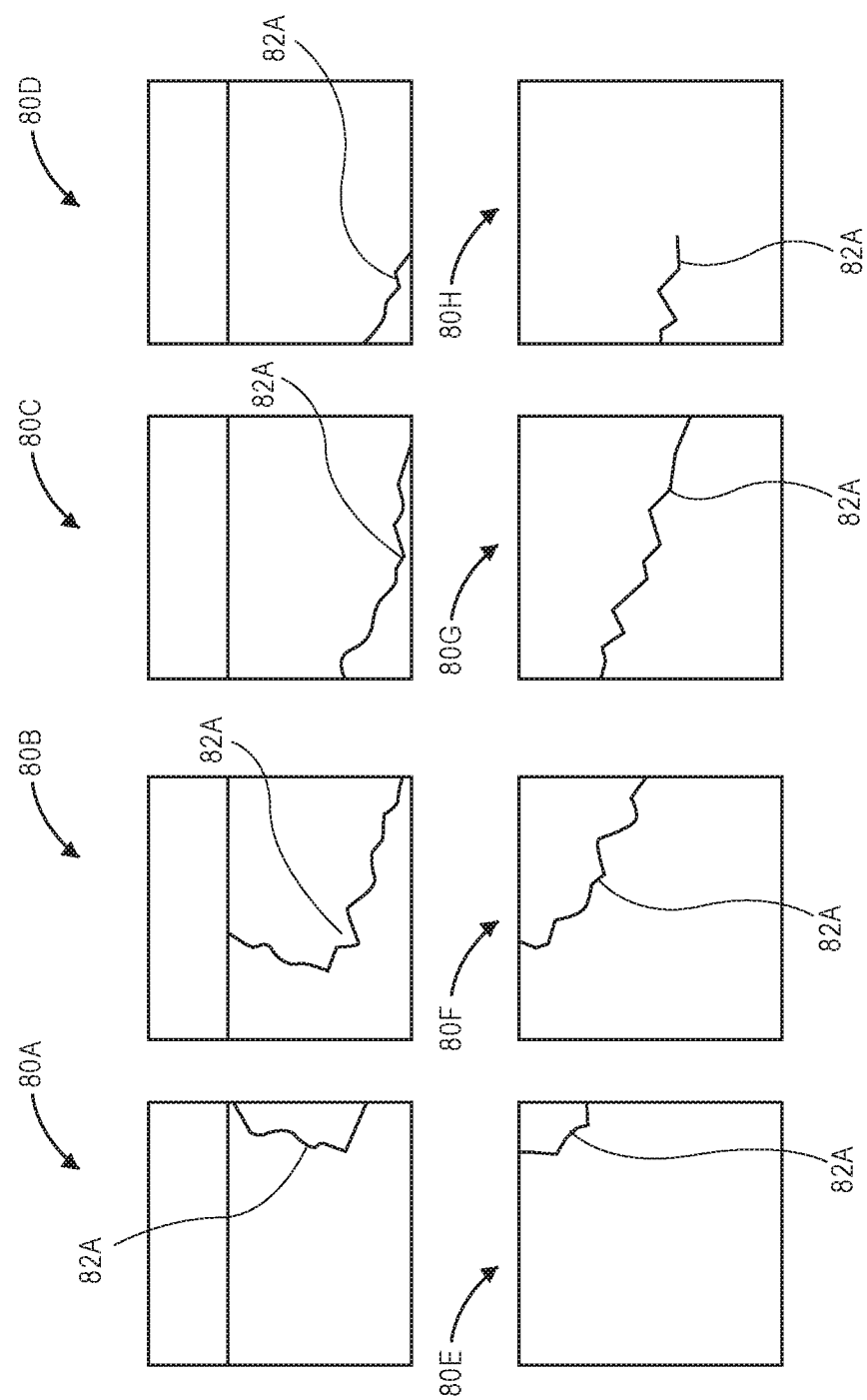

Once the patches 80$n$ have been extracted from an image of the subject 835, each of the patches may be processed to determine whether the respective patches depict any damage therein. For example, as is shown in FIGS. 8E and 8F, a plurality of patches 80A, 80B, 80C, 80D, 80E, 80F, 80G, 80H that are extracted from portions of the image 80 located near one end of the subject 835 are identified as including portions of the surface flaw 82A. Each of the patches 80A, 80B, 80C, 80D, 80E, 80F, 80G, 80H may be provided to a classifier, e.g., a convolutional neural network, that is trained to recognize surface flaws or other damage to subjects depicted within images.

Although FIGS. 8A through 8F are described with regard to extracting patches from images of subjects and using such patches to determine whether the subjects include one or more surface flaws or other damage, e.g., by providing such patches to a classifier trained to recognize surface flaws or other damage depicted therein, those of ordinary skill in the pertinent arts will recognize that patches may be similarly extracted from images and used to construct a data set for training such a classifier, or for validating that a classifier has been trained.

Figure 9:
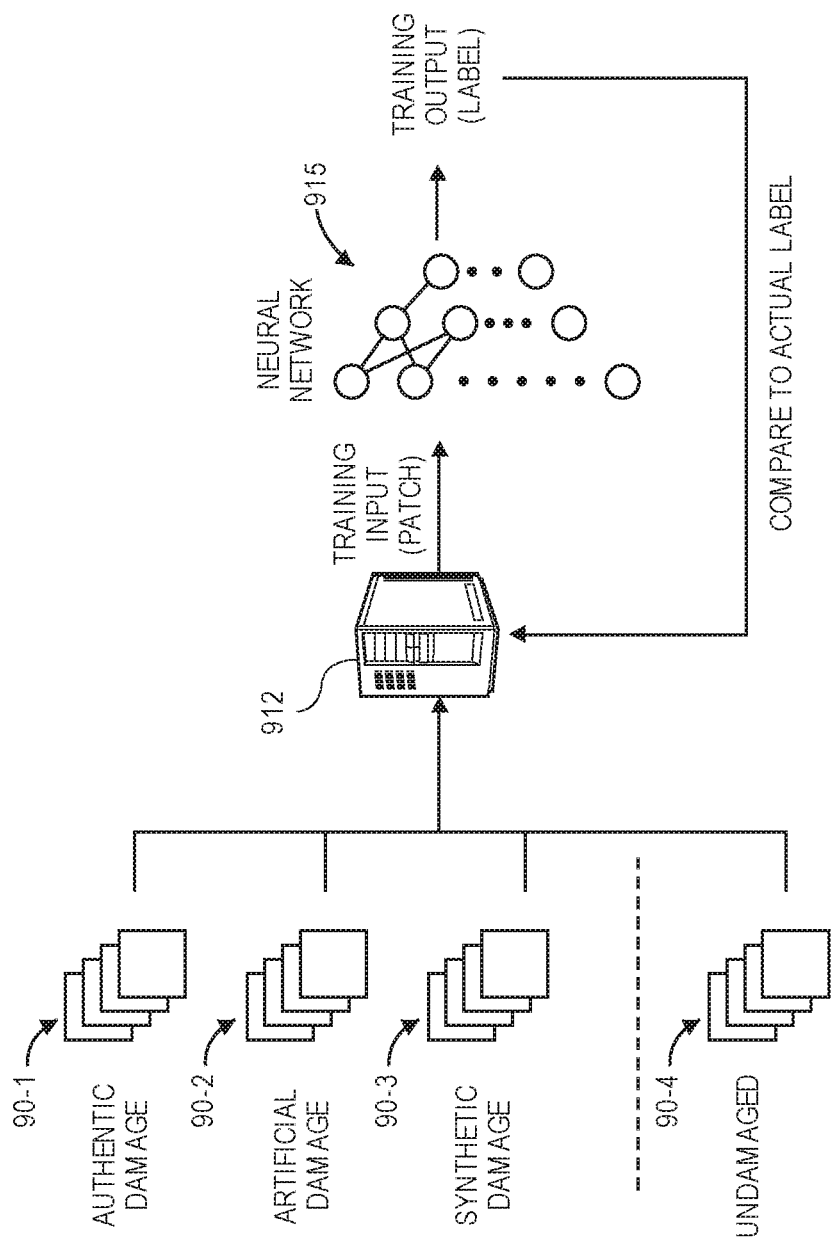
FIG. 9 is a view of aspects of one system for detecting surface flaws using computer vision in accordance with embodiments of the present disclosure.

Patches that have been extracted from images of authentically damaged subjects, artificially damaged subjects or undamaged subjects, or from images that have been synthetically altered to depict damage to subjects, may be labeled according to one or more annotation processes and used to train a classifier to recognize damage within images. Referring to FIG. 9, a view of aspects of one system for detecting flaws using computer vision in accordance with embodiments of the present disclosure is shown. Except where otherwise noted, reference numerals preceded by the number "9" shown in FIG. 9 indicate components or features that are similar to components or features having reference numerals preceded by the number "8" shown in FIGS. 8A through 8F, by the number "7" shown in FIG. 7, by the number "6" shown in FIG. 6, by the number "5" shown in FIG. 5, by the number "4" shown in FIG. 4A or 4B, by the number "2" shown in FIG. 2A or 2B or by the number "1" shown in FIG. 1A or 1B.

As is shown in FIG. 9, a server 912 operating a neural network 915 (e.g., a convolutional neural network) may train the neural network 915 by providing labeled patches of a training set to the neural network 915 as training inputs, and comparing outputs received from the neural network 915 as training outputs to the actual labels of such patches. For example, the training set may include a plurality of patches 90-1 of authentically damaged subjects, a plurality of patches 90-2 of artificially damaged subjects, a plurality of patches 90-3 that are synthetically altered to depict damages to subjects, and a plurality of patches 90-4 of undamaged subjects. Some or all of the pluralities of patches 90-1, 90-2, 90-3, 90-4 may be processed such as by increasing a level of contrast within such patches, rotating such patches by any angular extent (e.g., ninety degrees), or mirroring such patches, and the pluralities of the patches 90-1, 90-2, 90-3, 90-4 may be augmented to include patches for which a level of contrast was increased, rotated patches or mirrored patches. The testing of the neural network 915 may continue until an output received from the neural network 915 is sufficiently proximate the training outputs associated with the training inputs, e.g., the labels associated with such patches. Additionally, a validation set including labeled patches extracted from images of artificially damaged, authentically damaged and synthetically damaged subjects, as well as labeled patches extracted from images of undamaged subjects, may be used to determine whether the neural network 915 is adequately trained, or whether further training is necessary. The training set and the validation set may be subsets of a common data set of patches and labels, or may be entirely separate sets of patches and labels.

After a convolutional neural network has been trained to detect damages within subjects using labeled patches (or images) captured from authentically damaged subjects, as well as artificially damaged subjects, or subjects that have been synthetically damaged using image processing tools, along with labeled patches (or images) of unmanaged subjects, the trained classifier may be used to detect surface flaws or other damage depicted within patches (or images) of subjects such as propellers of aerial vehicles, or any other subjects. In some embodiments, such patches (or images) may be captured while the subjects are stationary or in motion, using imaging devices that are mounted with axes of orientation that are substantially transverse to one or more surfaces of the subjects, and while the subjects are illuminated using light sources from directionally diffuse light sources.

Figure 10:
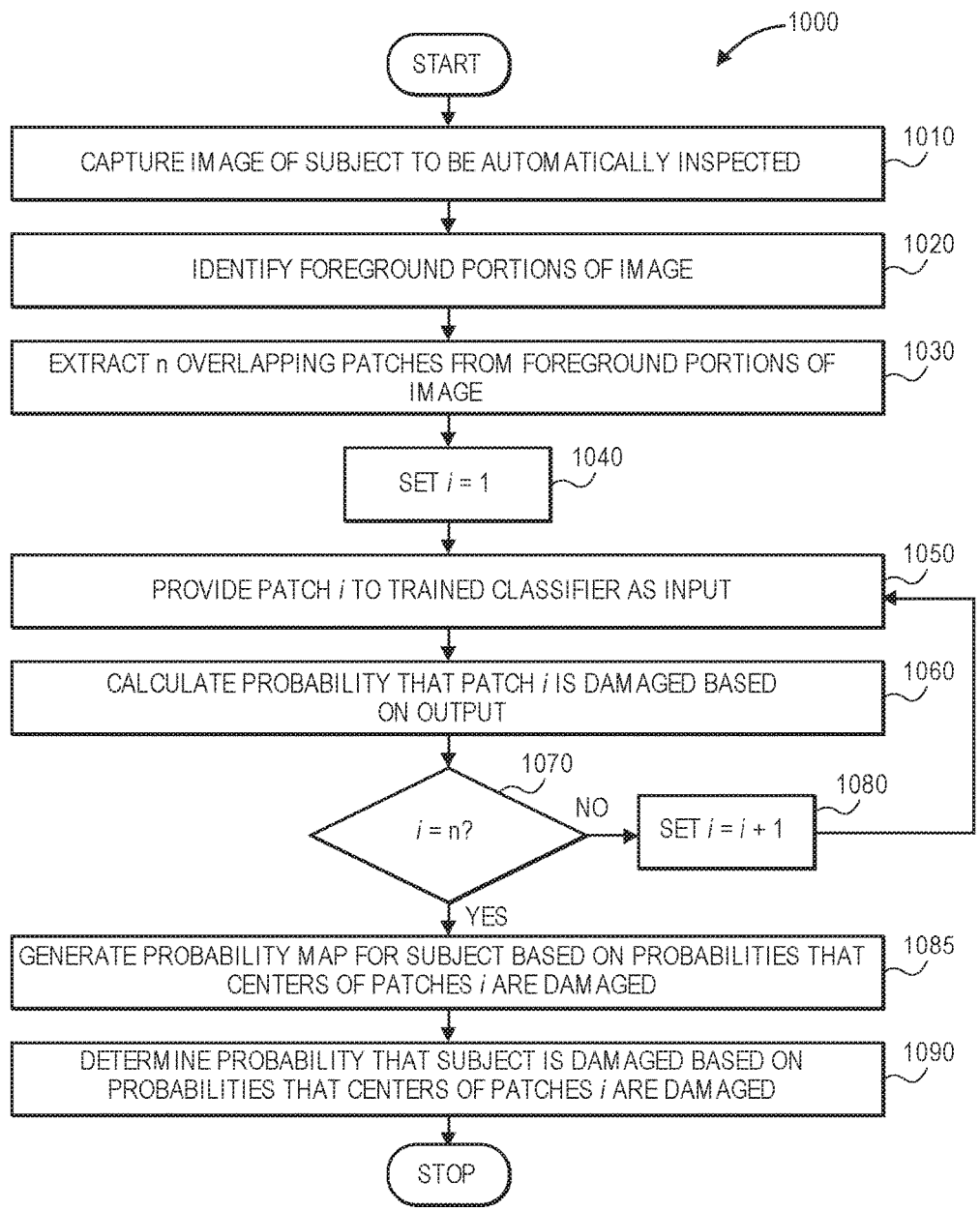
FIG. 10 is a flow chart of one process for detecting surface flaws using computer vision in accordance with embodiments of the present disclosure.

Referring to FIG. 10, a flow chart 1000 of one process for detecting surface flaws using computer vision in accordance with embodiments is shown. At box 1010, an image of a subject to be automatically inspected is captured by one or more imaging devices. For example, the image may have been captured in an imaging system or apparatus such as the imaging system 110 of FIG. 1A, by one or more of the imaging devices 140-1, 140-2. The image may be captured while the subject is stationary or in motion, and with the subject illuminated from one or more directions by light sources, such as the light sources 150-1, 150-2 of FIG. 1A, which may include a large number of lights or other illuminators that are arranged or disposed in a planar configuration. At box 1020, the foreground portions of the image are identified by any processes or techniques, such as adaptive thresholding, or Otsu binarization.

At box 1030, a plurality of n patches are extracted from the foreground portions of the images. As is discussed above, the n patches may have any dimensions and may overlap one another at any stride. For example, in some embodiments, the patches may have dimensions of approximately four hundred pixels by four hundred pixels, and may have a stride of approximately three hundred pixels. At box 1040, a value of a step variable i is set at 1, or i=1.

At box 1050, a patch i is provided to a trained classifier as an input. The patch may be selected at random from the n patches, or selected on some spatially dependent or relevant basis (e.g., according to an order from top to bottom, or from left to right). At box 1060, a probability that the patch i depicts damage is calculated based on an output from the trained classifier. For example, in some embodiments, the classifier may be trained to return an output indicative of a probability that damage is depicted anywhere within the patch i. Alternatively, in other embodiments, the classifier may be trained to return an output that a subset of the patch i, e.g., a central region of the patch i, depicts damage somewhere within the subset. For example, the central region may be defined with respect to a buffer within a barrier or boundary of the patch i. In some embodiments, a patch may have an area of four hundred pixels by four hundred pixels, and a trained classifier may evaluate a region of the patch having an area of three hundred pixels by three hundred pixels that is centered within the area of the patch.

At box 1070, whether each of the n patches has been evaluated by the trained classifier, or whether i=n, is determined. If each of the n patches has not been evaluated by the trained classifier, or if i is not equal to n, then the process advances to box 1080, where the value of i is incremented by one, or where i is set to equal i+1. The process then returns to box 1050, where another patch i is provided to the trained classifier as an input. If each of the n patches has been evaluated by the trained classifier, or if i is equal to n, then the process advances to box 1085, where a probability map for the subject is generated based on the probabilities that each of the patches i has been damaged.

At box 1090, a probability that the subject is damaged is determined based on the probabilities that each of the patches i has been damaged, and the process ends. For example, in order to conduct an image-level classification of the subject based on the patch-level classification, a maximum probability of damage determined for each of the n patches is assigned as a probability that the subject as a whole is damaged. Alternatively, a probability that the subject is damaged may be assessed based on an average (or mean) of the probabilities for each of the patches, a median of the probabilities, or any other statistical measure or technique. For example, a probability that the subject is damaged may be calculated based on a probability that a single patch depicts damage, such as where the probability exceeds a predetermined threshold. Alternatively, a probability that the subject is damaged may be calculated based on a number of the probabilities for each of such patches. For example, where a sufficiently large number of patches have probabilities that approach a predetermined threshold, a probability that the subject is damaged may be calculated accordingly even if none of the probabilities of the patches actually exceeds the threshold.

Figure 11:
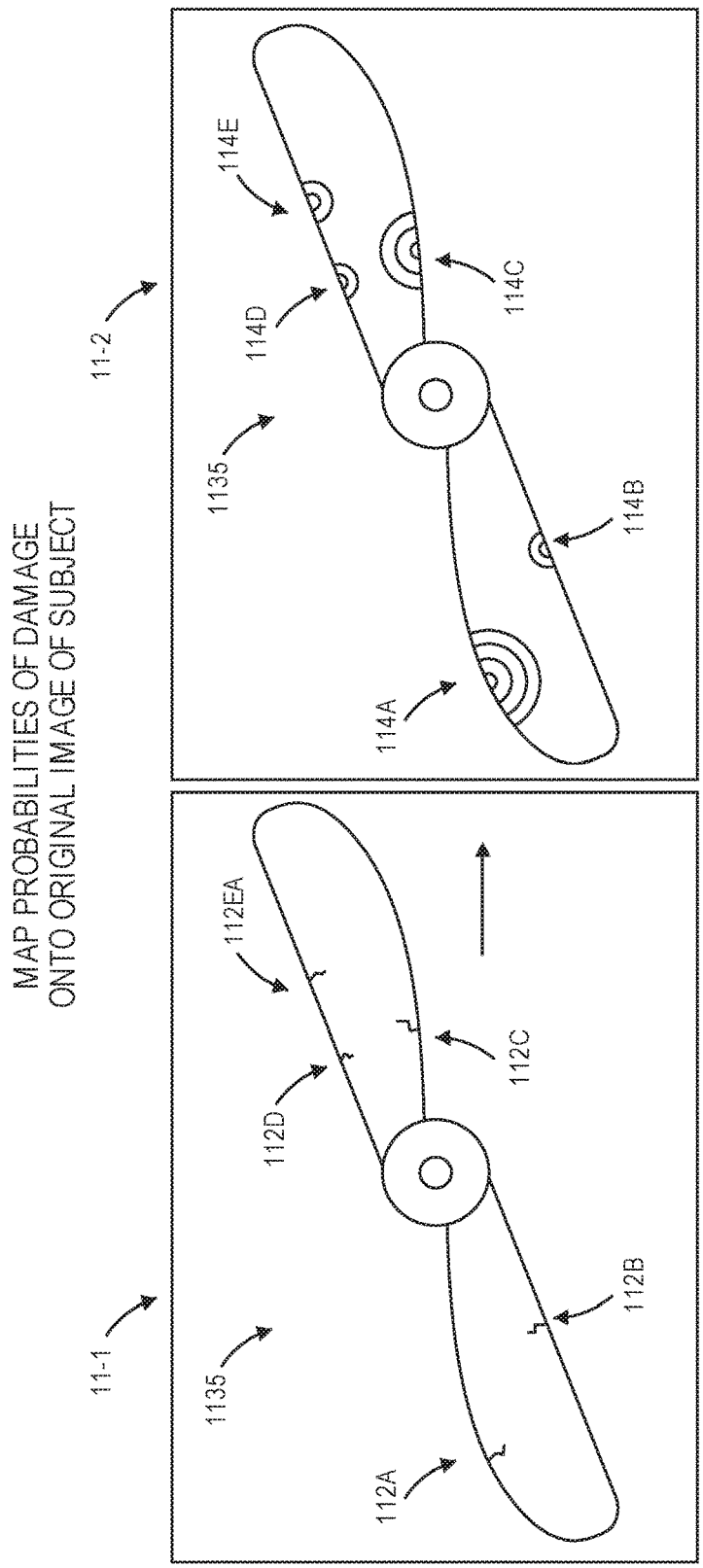
FIG. 11 is a view of aspects of one system for detecting surface flaws using computer vision in accordance with embodiments of the present disclosure.

Using outputs received from a trained classifier in response to patches extracted from an image of a subject, a visual representation of locations of damage to the subject may be superimposed upon the image of the subject. Referring to FIG. 11, a view of aspects of one system for detecting flaws using computer vision in accordance with embodiments of the present disclosure is shown. Except where otherwise noted, reference numerals preceded by the number "11" shown in FIG. 11 indicate components or features that are similar to components or features having reference numerals preceded by the number "9" shown in FIG. 9, by the number "8" shown in FIGS. 8A through 8F, by the number "7" shown in FIG. 7, by the number "6" shown in FIG. 6, by the number "5" shown in FIG. 5, by the number "4" shown in FIG. 4A or 4B, by the number "2" shown in FIG. 2A or 2B or by the number "1" shown in FIG. 1A or 1B.

As is shown in FIG. 11, probabilities that portions of a subject 1135 (viz., a propeller) are damaged may be determined based on outputs received from a trained classifier and used to signify, in a visual manner, which portions of the subject 1135 are damaged. For example, as is shown in FIG. 11, an image 11-1 is processed to determine whether the subject 1135 includes surface flaws 112A, 112B, 112C, 112D, 112E. A plurality of overlapping patches may be extracted from the image 11-1 and provided to a classifier trained to determine whether any of such patches depicts surface flaws or other damages. Outputs received from the classifier may include probabilities that a patch does, or does not, depict damage to the subject 1135. Values representative of such probabilities may be mapped onto an image 11-2 of the subject 1135, thereby resulting in a visual representation of the probabilities that specific locations 114A, 114B, 114C, 114D, 114E of the subject 1135 include surface flaws or other damages. The locations 114A, 114B, 114C, 114D, 114E may be color-coded or otherwise varied in emphasis to visually indicate likelihoods that such locations 114A, 114B, 114C, 114D, 114E include one or more surface flaws or other evidence of damage.

Although the disclosure has been described herein using exemplary techniques, components, and/or processes for implementing the systems and methods of the present disclosure, it should be understood by those skilled in the art that other techniques, components, and/or processes or other combinations and sequences of the techniques, components, and/or processes described herein may be used or performed that achieve the same function(s) and/or result(s) described herein and which are included within the scope of the present disclosure.

For example, although some of the embodiments disclosed herein reference the inspection of carbon fiber propellers intended for use on unmanned aerial vehicles, those of ordinary skill in the pertinent arts will recognize that the systems and methods disclosed herein are not so limited, and may be utilized in connection with the inspection of any type or form of subject that is formed from any type or form of material, and has any intended industrial, commercial, recreational or other use or purpose.

It should be understood that, unless otherwise explicitly or implicitly indicated herein, any of the features, characteristics, alternatives or modifications described regarding a particular embodiment herein may also be applied, used, or incorporated with any other embodiment described herein, and that the drawings and detailed description of the present disclosure are intended to cover all modifications, equivalents and alternatives to the various embodiments as defined by the appended claims. Moreover, with respect to the one or more methods or processes of the present disclosure described herein, including but not limited to the processes represented in the flow charts of FIG. 3 or 10, orders in which such methods or processes are presented are not intended to be construed as any limitation on the claimed inventions, and any number of the method or process steps or boxes described herein can be combined in any order and/or in parallel to implement the methods or processes described herein. Also, the drawings herein are not drawn to scale.

Conditional language, such as, among others, "can," "could," "might," or "may," unless specifically stated otherwise, or otherwise understood within the context as used, is generally intended to convey in a permissive manner that certain embodiments could include, or have the potential to include, but do not mandate or require, certain features, elements and/or steps. In a similar manner, terms such as "include," "including" and "includes" are generally intended to mean "including, but not limited to." Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment.

Disjunctive language such as the phrase "at least one of X, Y, or Z," or "at least one of X, Y and Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a" or "an" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B and C" can include a first processor configured to carry out recitation A working in conjunction with a second processor configured to carry out recitations B and C.

Language of degree used herein, such as the terms "about," "approximately," "generally," "nearly" or "substantially" as used herein, represent a value, amount, or characteristic close to the stated value, amount, or characteristic that still performs a desired function or achieves a desired result. For example, the terms "about," "approximately," "generally," "nearly" or "substantially" may refer to an amount that is within less than 10% of, within less than 5% of, within less than 1% of, within less than 0.1% of, and within less than 0.01% of the stated amount.

Although the invention has been described and illustrated with respect to illustrative embodiments thereof, the foregoing and various other additions and omissions may be made therein and thereto without departing from the spirit and scope of the present disclosure.

What is claimed is:

1. A system comprising:
a first imaging device having a first axis of orientation;
a second imaging device having a second axis of orientation, wherein the first axis of orientation is substantially parallel to the second axis of orientation, and wherein the first axis of orientation is substantially opposite to the second axis of orientation;
a first light source, wherein the first light source comprises a first plurality of illuminators distributed in a first planar configuration;
a second light source, wherein the second light source comprises a second plurality of illuminators distributed in a second planar configuration, and wherein an angle between a first axis normal to the first planar configuration and a second axis normal to the second planar configuration is greater than or equal to forty-five degrees;
at least one data store; and
at least one computer processor configured to at least:
capture a first image of the first subject by the first imaging device, wherein the first axis of orientation is substantially perpendicular to a first surface of the first subject, and wherein the first image is captured with light projected upon at least the first surface of the first subject by the first light source;
capture a second image of the first subject by the second imaging device, wherein the second axis of orientation is substantially perpendicular to a second surface of the first subject, and wherein the first image is captured with light projected upon at least the second surface of the first subject by the second light source;
extract at least a first plurality of patches from the first image, wherein each of the first plurality of patches overlaps at least one of the first plurality of patches;
extract at least a second plurality of patches from the second image, wherein each of the second plurality of patches overlaps at least one of the second plurality of patches;
provide a plurality of inputs to a convolutional neural network trained to detect damage within an image of a subject, wherein each of the plurality of inputs is one of the first plurality of patches or one of the second plurality of patches;
receive a plurality of outputs from the convolutional neural network, wherein each of the outputs is a probability that one of the first plurality of patches or one of the second plurality of patches depicts damage to the first subject; and
calculate a probability that the first subject is damaged based at least in part on the plurality of outputs.

2. The system of claim 1, wherein the at least one computer processor is further configured to at least:
extract the plurality of outputs from at least one convolutional layer of the convolutional neural network;
perform batch normalizations on each of the plurality of outputs;
apply bilinear pooling operations on each of the plurality of outputs; and
calculate probabilities that each of the first plurality of patches and each of the second plurality of patches depicts damage to the first surface of the first subject or the second surface of the first subject by a fully connected softmax layer of the convolutional neural network.

3. The system of claim 2, wherein the at least one computer processor is further configured to at least:
generate a visual representation of at least some of the probabilities on the first image, wherein the visual representation comprises a visual indicator of at least one of the probabilities calculated for one of the first plurality of patches in at least one location on the first surface corresponding to the one of the first plurality of patches.

4. A method to inspect a subject, wherein the method comprises:
identifying a data set comprising a plurality of images and a plurality of labels, wherein each of the labels corresponds to one of the plurality of images, and wherein each of the labels is one of damaged or undamaged;
training a classifier to detect damage to subjects depicted within images using at least some of the plurality of images of the data set and at least some of the plurality of labels of the data set;
capturing a first image of the subject within an imaging system comprising a first imaging device and a first planar light source, wherein the first imaging device has a first axis of orientation aligned substantially transverse to at least a portion of a first surface of the subject, wherein the first image is captured with the first planar light source projecting light onto at least a portion of the first surface of the subject, and wherein the subject is fixedly or rotatably positioned with the first surface of the subject within at least a first field of view of the first imaging device;
extracting a first plurality of patches from the first image of the subject, wherein each of the first plurality of patches overlaps at least another of the first plurality of patches;
providing at least a first patch of the first plurality of patches to the classifier as at least a first input;
receiving at least a first output from the classifier based at least in part on the first input;
determining a probability that at least the first patch depicts damage to at least the first surface of the subject based at least in part on the first output; and
determining a probability that the subject is damaged based at least in part on the probability that at least the first patch depicts damage to at least the first surface of the subject.

5. The method of claim 4, further comprising:
identifying at least one authentically damaged subject, wherein the at least one authentically damaged subject was damaged during an operation of the subject in accordance with at least one standard operating procedure associated with the authentically damaged subject;
capturing at least one image of the at least one authentically damaged subject;
associating a label of damaged with the at least one image; and
adding the at least one image and the label to the data set.

6. The method of claim 4, further comprising:
manually or automatically imparting damage to at least one surface of at least one subject;
after manually or automatically imparting damage to the at least one surface of the at least one subject, capturing at least one image of the at least one subject;
associating a label of damaged with the at least one image; and
adding the at least one image and the label to the data set.

7. The method of claim 4, further comprising:
capturing at least one image of at least one subject;
altering at least a portion of the at least one image to include a visual indication of damage to at least one surface of the at least one subject;
associating a label of damaged with the at least one image; and
adding the at least one image and the label to the data set.

8. The method of claim 4, wherein the classifier is a convolutional neural network.

9. The method of claim 8, wherein receiving at least the first output from the classifier based at least in part on the first input comprises:
extracting the first output from at least one convolutional layer of the convolutional neural network;
performing a batch normalization to the first output; and
applying a bilinear pooling operation on the first output, and
wherein determining the probability that at least the first patch depicts damage to at least the first surface of the subject based at least in part on the first output comprises:
determining the probability that at least the first patch depicts damage to at least the first surface of the subject by a fully connected softmax layer of the convolutional neural network.

10. The method of claim 4, wherein each of the first plurality of patches has a size of approximately four hundred pixels by four hundred pixels, and
wherein the first plurality of patches overlap one another by a stride of approximately three hundred pixels.

11. The method of claim 10, wherein determining the probability that at least the first patch depicts damage to at least the first surface of the subject comprises:
determining a probability that a subset of the first patch depicts damage to the subject,
wherein the subset has an area of approximately three hundred pixels by three hundred pixels.

12. The method of claim 4, further comprising:
detecting a background region of the first image by adaptive thresholding; and
identifying a foreground region of the first image based at least in part on the background region,
wherein at least some of the first plurality of patches are extracted from the foreground region of the first image.

13. The method of claim 4, wherein capturing the image of the subject by at least the first imaging device comprises:
illuminating at least the first surface of the subject by at least one light source, wherein the at least one light source comprises a plurality of illuminators distributed in a planar configuration, and
wherein the image of the subject is captured while at least the first surface of the subject is illuminated by the at least one light source.

14. The method of claim 4, wherein the imaging system further comprises a second imaging device and a second planar light source,
wherein the second imaging device has a second axis of orientation aligned substantially transverse to at least a portion of a second surface of the subject,
wherein the second planar light source is aligned to project light onto at least a portion of the second surface of the subject, and
wherein the subject is fixedly or rotatably mounted with at least the second surface of the subject within at least a second field of view of the second imaging device.

15. The method of claim 4, wherein providing at least the first patch of the first plurality of patches to the classifier as at least the first input comprises:
providing at least some of the first plurality of patches to the classifier as inputs, wherein the first input is one of the inputs,
wherein receiving at least the first output from the classifier based at least in part on the first input comprises:
receiving outputs from the classifier, wherein each of the first outputs is based at least in part on one of the inputs, and wherein the first output is one of the outputs,
wherein determining the probability that at least the first patch depicts damage to at least the first surface of the subject based at least in part on the first output comprises:
determining probabilities that each of the at least some of the first plurality of patches depicts damage to at least a portion of the first surface of the subject based at least in part on the outputs,
wherein the probability that the subject is damaged is at least one of:
a maximum value of the probabilities;
a mean value of the probabilities; or
a median value of the probabilities.

16. The method of claim 4, wherein the subject is a propeller configured for use aboard an aerial vehicle.

17. The method of claim 4, wherein the subject is formed from at least one of carbon fiber, graphite, machined aluminum, titanium, fiberglass, wood or plastic.

18. A system comprising:
a first planar light source comprising a first plurality of illuminators arranged in a first planar configuration;
a second planar light source comprising a second plurality of illuminators arranged in a second planar configuration, wherein a first axis normal to the first planar configuration is at an angle of greater than or equal to forty-five degrees with respect to a second axis normal to the second planar configuration;
an imaging device having an axis of orientation and a field of view, wherein the axis of orientation is aligned substantially vertically, and wherein the field of view is aligned in a substantially downward orientation;
a subject mount configured for fixedly or rotatably mounting to a hub of a propeller within the field of view; and
a computing device having at least one computer processor,
wherein the computing device is configured to operate a convolutional neural network.

19. The system of claim 18, wherein the computing device is further configured to at least:
capture a first image of a first propeller, wherein at least a portion of the first propeller includes at least one surface flaw incurred during normal operation of the first propeller;
assign a first label of damaged to the first image;
capture a second image of a second propeller, wherein at least a portion of the second propeller includes at least one surface flaw manually or automatically imparted upon the portion of the second propeller;
assign a second label of damaged to the second image;

capture a third image of a third propeller, wherein the third propeller is substantially undamaged;
synthetically alter the third image to depict a visual representation of at least one surface flaw on at least a portion of the third propeller;
assign a third label of damaged to the synthetically altered third image;
capture a fourth image of a fourth propeller, wherein the fourth propeller is substantially undamaged;
assign a fourth label of undamaged to the fourth image;
define a data set comprising at least a portion of the first image, at least a portion of the second image, at least a portion of the synthetically altered third image, at least a portion of the fourth image, the first label, the second label, the third label and the fourth label; and
train the convolutional neural network to recognize damage in images of subjects based at least in part on at least some of the data set.

20. The system of claim 19, wherein the computing device is further configured to at least:
capture, by the imaging device, a fifth image of at least one blade of a fifth propeller;
identify a foreground portion of the fifth image;
extract a plurality of patches from the foreground portion of the fifth image, wherein each of the plurality of patches overlaps at least one of the plurality of patches;
provide a plurality of inputs to the convolutional neural network trained to detect damage within an image of a subject, wherein each of the plurality of inputs is one of the plurality of patches;
extract a plurality of outputs from at least one convolutional layer of the convolutional neural network;
perform batch normalizations on each of the plurality of outputs;
apply bilinear pooling operations on each of the plurality of outputs;
calculate probabilities that each of the plurality of patches depicts damage to the at least one blade surface of the fifth propeller by a fully connected softmax layer of the convolutional neural network; and
calculate a probability that the fifth propeller is damaged based at least in part on the probabilities that each of the plurality of patches depicts damage.

* * * * *